United States Patent
Sterling et al.

(10) Patent No.: US 7,009,180 B2
(45) Date of Patent: Mar. 7, 2006

(54) PATHLENGTH-INDEPENDENT METHODS FOR OPTICALLY DETERMINING MATERIAL COMPOSITION

(75) Inventors: Bernhard B. Sterling, Sunnyvale, CA (US); James R. Braig, Piedmont, CA (US); Daniel S. Goldberger, Boulder, CO (US); Philip C. Hartstein, Cupertino, CA (US); Robert D. Gaffney, Atherton, CA (US)

(73) Assignee: Optiscan Biomedical Corp., Alameda, CA (US)

( * ) Notice: Subject to any disclaimer, the term of this patent is extended or adjusted under 35 U.S.C. 154(b) by 306 days.

(21) Appl. No.: 10/319,409

(22) Filed: Dec. 12, 2002

(65) Prior Publication Data

US 2003/0178569 A1    Sep. 25, 2003

Related U.S. Application Data

(60) Provisional application No. 60/357,264, filed on Feb. 12, 2002, provisional application No. 60/341,435, filed on Dec. 14, 2001.

(51) Int. Cl.
G01N 21/35    (2006.01)

(52) U.S. Cl. .......................... 250/339.12; 250/339.09; 250/343

(58) Field of Classification Search ........... 250/339.09, 250/339.1, 339.11, 341.1, 341.5, 341.8, 343, 250/338.5; 356/39, 40, 41
See application file for complete search history.

(56) References Cited

U.S. PATENT DOCUMENTS

| | | | |
|---|---|---|---|
| 3,787,124 A | 1/1974 | Lowy et al. | |
| 4,350,441 A | 9/1982 | Wicnienski | |
| 4,397,956 A | 8/1983 | Maggio | |
| 4,655,225 A | 4/1987 | Dähne et al. | |
| 4,730,112 A | 3/1988 | Wong | |
| 4,819,752 A | 4/1989 | Zelin | |
| 5,081,998 A | 1/1992 | Yelderman et al. | |
| 5,111,817 A | 5/1992 | Clark et al. | |
| 5,204,532 A | 4/1993 | Rosenthal | |
| 5,277,181 A | 1/1994 | Mendelson et al. | |
| 5,348,003 A | 9/1994 | Caro | |
| 5,361,758 A | 11/1994 | Hall et al. | |
| 5,370,114 A | 12/1994 | Wong et al. | |
| 5,372,136 A | 12/1994 | Steuer et al. | |
| 5,377,674 A | 1/1995 | Kuestner | |
| 5,379,764 A | 1/1995 | Barnes et al. | |
| 5,412,581 A | 5/1995 | Tackett | |
| 5,452,716 A | 9/1995 | Clift | |
| 5,481,113 A | 1/1996 | Dou et al. | |
| 5,576,544 A | 11/1996 | Rosenthal | |
| 5,596,992 A * | 1/1997 | Haaland et al. ............. | 600/473 |

(Continued)

FOREIGN PATENT DOCUMENTS

EP    0 982 582 A1    8/1998

(Continued)

OTHER PUBLICATIONS

International Search Report PCT/US03/04548 dated Sep. 23, 2003 in 5 pages.

(Continued)

*Primary Examiner*—Albert Gagliardi
(74) *Attorney, Agent, or Firm*—Knobbe Martens Olson & Bear, LLP

(57) ABSTRACT

A method uses spectroscopy to determine an analyte concentration in a sample. The method includes producing an absorbance spectrum of the sample. The method further includes shifting the absorbance spectrum to zero in a wavelength region. The method further includes subtracting a water or other substance contribution from the absorbance spectrum.

45 Claims, 28 Drawing Sheets

U.S. PATENT DOCUMENTS

| | | | |
|---|---|---|---|
| 5,606,164 | A | 2/1997 | Price et al. |
| 5,615,673 | A * | 4/1997 | Berger et al. ............... 600/326 |
| 5,655,530 | A | 8/1997 | Messerschmidt |
| 5,692,503 | A | 12/1997 | Kuenstner |
| 5,713,353 | A | 2/1998 | Castano |
| 5,720,284 | A | 2/1998 | Aoyagi et al. |
| 5,725,480 | A | 3/1998 | Oosta et al. |
| 5,773,301 | A | 6/1998 | Ziegler |
| 5,823,951 | A | 10/1998 | Messerschmidt |
| 5,857,462 | A | 1/1999 | Thomas et al. |
| 5,900,632 | A | 5/1999 | Sterling et al. |
| 5,933,792 | A | 8/1999 | Andersen et al. |
| 6,040,578 | A | 3/2000 | Malin et al. |
| 6,067,463 | A | 5/2000 | Jeng et al. |
| 6,087,182 | A | 7/2000 | Jeng et al. |
| 6,115,673 | A | 9/2000 | Malin et al. |
| 6,121,050 | A | 9/2000 | Han |
| 6,124,134 | A | 9/2000 | Stark |
| 6,157,041 | A | 12/2000 | Thomas et al. |
| 6,161,028 | A | 12/2000 | Braig et al. |
| 6,198,949 | B1 | 3/2001 | Braig et al. |
| 6,236,047 | B1 | 5/2001 | Malin et al. |
| 6,262,798 | B1 | 7/2001 | Shepard et al. |
| 6,285,448 | B1 | 9/2001 | Kuenster |
| 6,330,058 | B1 * | 12/2001 | Garcia-Rubio et al. ....... 356/39 |
| 6,426,045 | B1 | 7/2002 | Jeng et al. |
| 6,580,934 | B1 | 6/2003 | Braig et al. |
| 6,694,157 | B1 * | 2/2004 | Stone et al. ................. 600/310 |
| 6,862,534 | B1 * | 3/2005 | Sterling et al. ............... 702/23 |
| 2003/0031597 | A1 * | 2/2003 | Sota et al. ............... 422/82.09 |
| 2003/0160961 | A1 * | 8/2003 | Hafeman et al. ........... 356/433 |

FOREIGN PATENT DOCUMENTS

| | | |
|---|---|---|
| EP | 0982582 A | 3/2000 |
| WO | WO 93/13706 | 7/1993 |
| WO | WO 99/39631 | 8/1999 |
| WO | WO 01/30236 | 5/2001 |
| WO | PCT/US 02/40133 | 12/2002 |

OTHER PUBLICATIONS

International Search Report PCT/US02/40133 dated Apr. 23, 2003 in 7 pages.

R. Anthony Shaw et al., "Infrared Spectroscopy in Clinical and Diagnostic Analysis," Encyclopedia of Analytical Chemistry, pp 1-20.

Günter Janatsch et al., "Multivariate Calibration for Assays in Clinical Chemistry Using Attenuated Total Reflection Infrared Spectra of Human Blood Plasma," Analytical Chemistry, 1989, 61, pp 2016-2023.

Kenneth J. Ward et al., "Post-Prandial Blood Glucose Determination by Quantitative Mid-Infrared Spectroscopy," Applied Spectroscopy, vol. 46, No. 6, 1992, pp 959-965.

F. De Lène Mirouze, et al., "Quantitative Analysis of Glucose Syrups by ATR/FT-IR Spectroscopy," Applied Spectroscopy, vol. 47, No. 8, 1993, pp 1187-1191.

H.M. Heise et al., "Multicomponent Assay for Blood Substrates in Human Plasma by Mid-Infrared Spectroscopy and its Evaluation for Clinical Analysis," Applied Spectroscopy, vol. 48, No. 1, 1994, pp 85-95.

K.H. Norris et al., "Rapid Measurement of Analytes in Whole Blood with NIR Transmittance," Leaping Ahead with Near Infrared Spectroscopy, 1995, pp 432-436.

J. Todd Kuenstner et al., "Spectrophotometry of Human Hemoglobin in the Midinfrared Region," 1997, pp 225-232.

Michael J. McShane et al, "Near-Infrared Spectroscopy for Determination of Glucose, Lactate, and Ammonia in Cell Culture Media," Applied Spectroscopy, vol. 52, No. 8, 1998, pp 1073-1078.

Jason J. Burmeister et al., "Spectroscopic Considerations for Noninvasive Blood Glucose Measurements with Near Infrared Spectroscopy," IEEE Infrared Spectroscopy Newsletter, Apr. 1998, pp 1-5.

Cyril Petibois et al., "Glucose and Lactate Concentration Determination on Single Microsamples by Fourier-Transform Infrared Spectroscopy," INSERM U 443, Equipe deChimie Bio-Organique, Oct. 1999, pp 210-215.

Christopher B. Lewis et al., Investigation of Near-Infrared Spectroscopy for Periodic Determination of Glucose in Cell Culture Media in Situ, Applied Spectroscopy, vol. 54, No. 10, 2000, pp 1453-1457.

Ken-ichiro Kajiwara et al., Spectroscopic Quantitative Analysis of Blood Glucose by Fourier Transform Infrared Spectroscopy with an Attenuated Total Reflection Prism, Medical Progress through Technology 18,No. 3, 1992, Dordrecht, NL, pp 181-189.

Ham, Fredric M., et al., Determination of Glucose Concentrations in an Aqueous Matrix from NIR Spectra Using Optimal Time-Domain Filtering and Partial Least-Squares Regression, IEEE Transactions on Biomedical Engineering, vol. 44, No. 6, Jun. 1997, pp. 475-485.

Percherancier, J.P., et al., Fourier Transform Infrared (FT-IR) Spectrometry to Detect Additives and Contaminants in Insulating Oils, IEEE Electrical Insulation Magazine, vol. 14, No. 3, May/Jun. 1998, pp. 23-29.

* cited by examiner

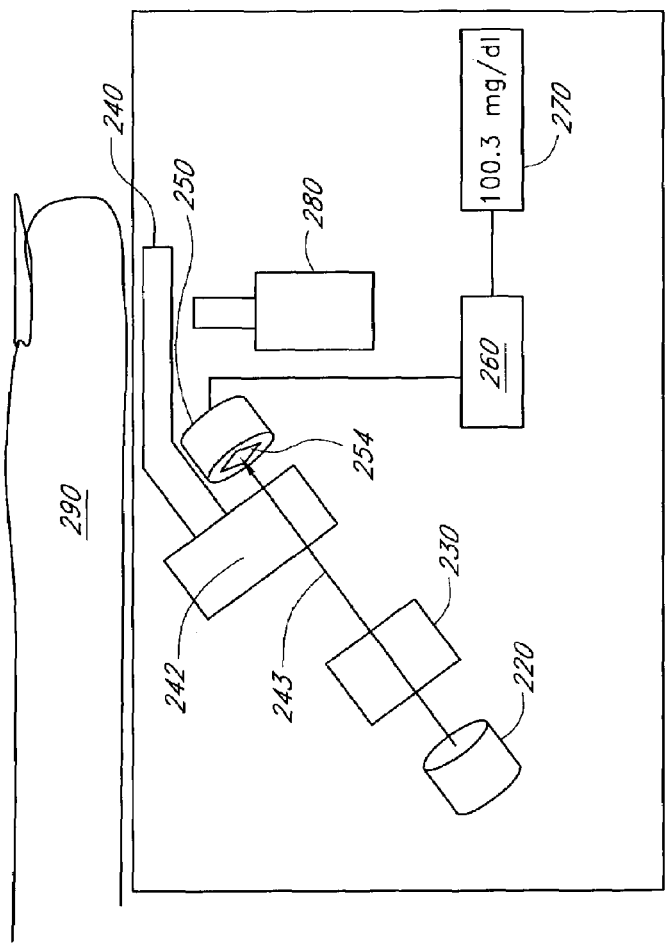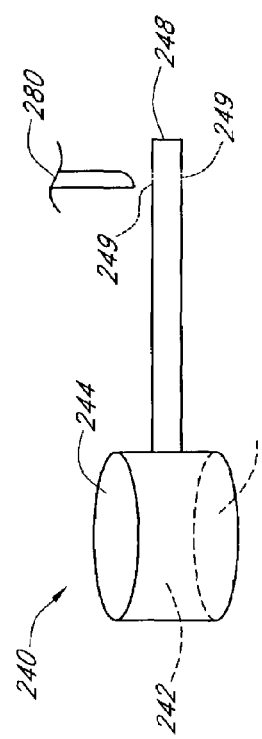
FIG. 13
FIG. 14

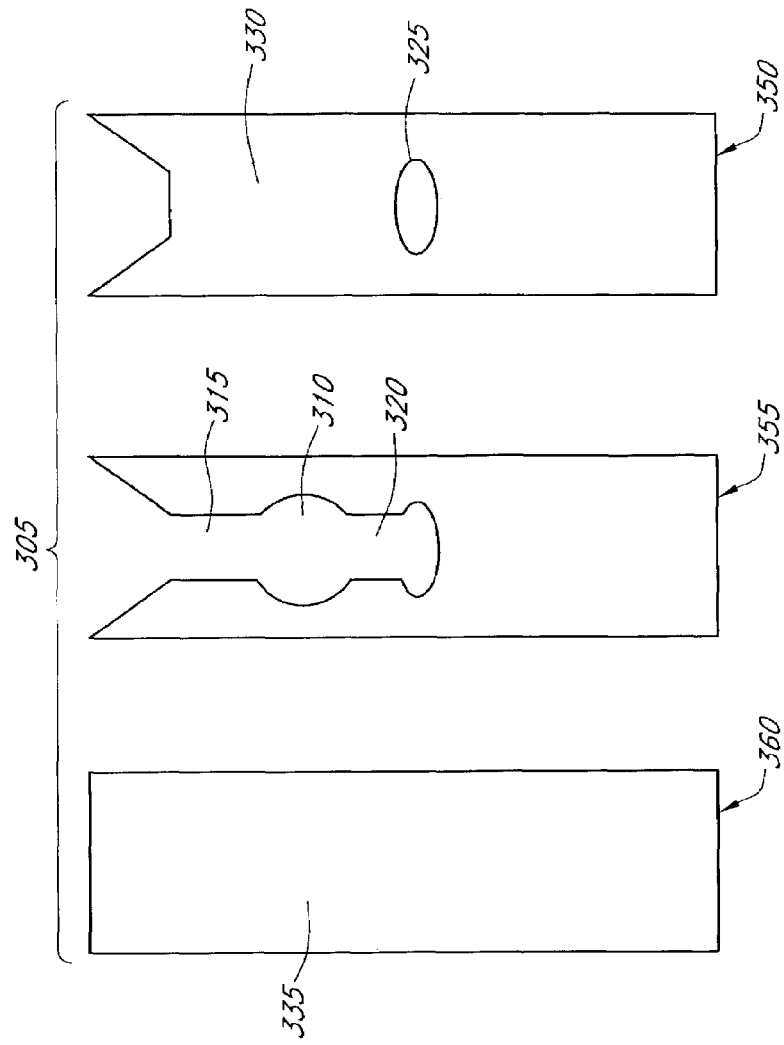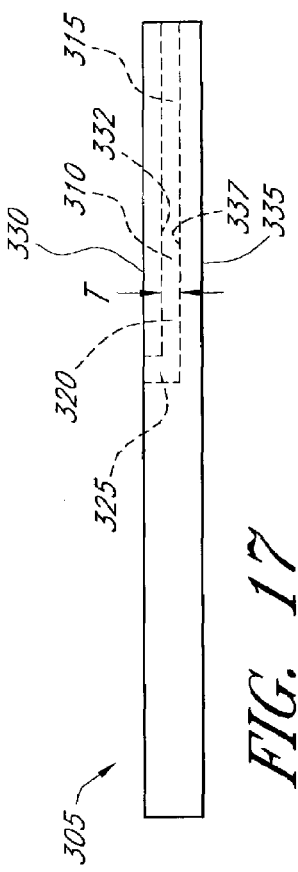
FIG. 15  FIG. 16  FIG. 17

PATHLENGTH-INDEPENDENT METHODS FOR OPTICALLY DETERMINING MATERIAL COMPOSITION

CLAIM OF PRIORITY

This application claims priority to U.S. Provisional Patent Application No. 60/341,435 filed Dec. 14, 2001 and U.S. Provisional Patent Application No. 60/357,264 filed Feb. 12, 2002, both of which are incorporated in their entireties by reference herein.

BACKGROUND OF THE INVENTION

1. Field of the Invention

The disclosure herein relates generally to methods for determining the composition of a material sample by analyzing infrared energy that has been passed through or emitted from the material sample.

2. Description of the Related Art

When taking measurements of a sample of blood (or other materials) in order to assess a particular aspect such as glucose content, a number of problems are realized. A sample is collected in/on a test strip, or cuvette, or perhaps by a noninvasive means, whereby a source is applied to the blood sample (or tissue in a noninvasive sense) and the constituents can be analyzed. When the initial readings are taken, many blood analytes appear in the data and the next step is to identify which reading correlates to each particular constituent to identify and quantify the blood analyte of interest.

For example, a measurement of a blood sample is taken and the focus is to measure blood glucose in such a way as to identify its content and to predict its trend (rising, falling, or sustained). When the sample is measured all sorts of variables influence the data. To obtain accurate measurements it is helpful to understand which constituents are present in the data set, understand their effects on the analyte that is being measured (such as glucose), and correct for any differences that intrinsic and measuring-device-related variables may cause.

SUMMARY OF THE INVENTION

In certain embodiments, a method uses spectroscopy to determine an analyte concentration in a sample. The method comprises producing an absorbance spectrum of the sample. The method further comprises shifting the absorbance spectrum to zero in a wavelength region. The method further comprises subtracting a water or other substance contribution from the absorbance spectrum.

In certain other embodiments, a method provides pathlength insensitive measurements of blood constituents in a sample using infrared (IR) spectroscopy. The method comprises providing an absorbance spectrum of the sample. The method further comprises shifting the absorbance spectrum to zero at an isosbestic wavelength, wherein water and protein within the sample have approximately equivalent absorptions at the isosbestic wavelength.

BRIEF DESCRIPTION OF THE DRAWINGS

FIG. 13 is a schematic view of a reagentless whole-blood detection system.

FIG. 14 is a perspective view of one embodiment of a cuvette for use with the reagentless whole-blood detection system.

FIG. 15 is a plan view of another embodiment of a cuvette for use with the reagentless whole-blood detection system.

FIG. 16 is a disassembled plan view of the cuvette shown in FIG. 15.

FIG. 17 is a side view of the cuvette of FIG. 15.

DETAILED DESCRIPTION OF THE PREFERRED EMBODIMENT

Figure 1:
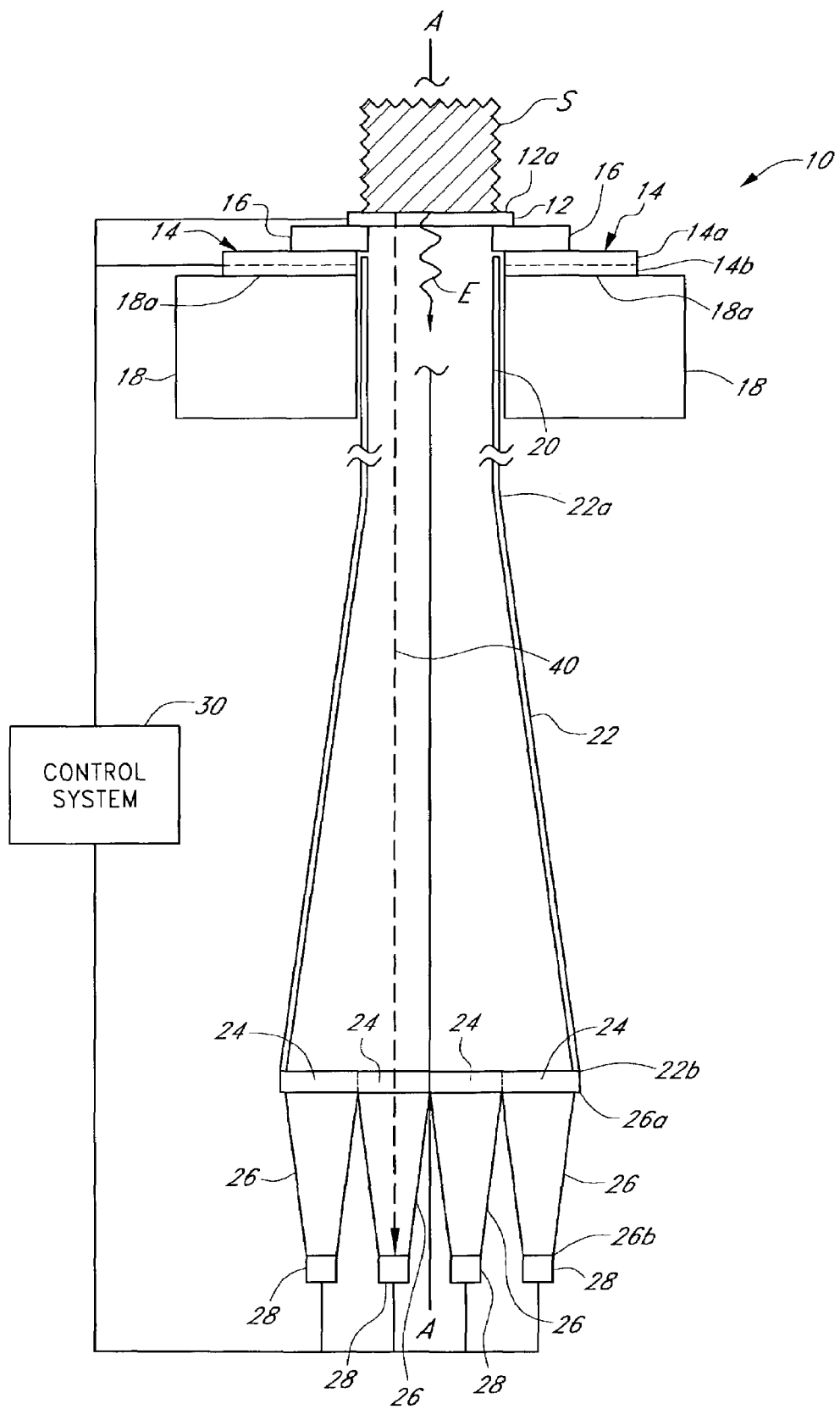
FIG. 1 is a schematic view of a noninvasive optical detection system.

Although certain preferred embodiments and examples are disclosed below, it will be understood by those skilled in the art that the invention extends beyond the specifically disclosed embodiments to other alternative embodiments and/or uses of the invention and obvious modifications and equivalents thereof. Thus, it is intended that the scope of the invention herein disclosed should not be limited by the particular disclosed embodiments described below.

Embodiments are described herein using flow diagrams that have steps in a particular order, and the order of the steps in the flow diagrams are not to be considered to be limiting. Other methods with different orders of steps are also compatible with embodiments described herein. In addition, other methods with additional steps are also compatible with embodiments described herein.

I. Overview of Analyte Detection Systems

Disclosed herein are analyte detection systems, including a noninvasive system discussed largely in part A below and a whole-blood system discussed largely in part B below. Also disclosed are various methods, including methods for detecting the concentration of an analyte in a material sample. Both the noninvasive system/method and the whole-blood system/method can employ optical measurement. As used herein with reference to measurement apparatus and methods, "optical" is a broad term and is used in its ordinary sense and refers, without limitation, to identification of the presence or concentration of an analyte in a material sample without requiring a chemical reaction to take place. As discussed in more detail below, the two approaches each can operate independently to perform an optical analysis of a material sample. The two approaches can also be combined in an apparatus, or the two approaches can be used together to perform different steps of a method.

In one embodiment, the two approaches are combined to perform calibration of an apparatus, e.g., of an apparatus that employs a noninvasive approach. In another embodiment, an advantageous combination of the two approaches performs an invasive measurement to achieve greater accuracy and a whole-blood measurement to minimize discomfort to the patient. For example, the whole-blood technique may be more accurate than the noninvasive technique at certain times of the day, e.g., at certain times after a meal has been consumed, or after a drug has been administered.

It should be understood, however, that any of the disclosed devices may be operated in accordance with any suitable detection methodology, and that any disclosed method may be employed in the operation of any suitable device. Furthermore, the disclosed devices and methods are applicable in a wide variety of situations or modes of operation, including but not limited to invasive, noninvasive, intermittent or continuous measurement, subcutaneous implantation, wearable detection systems, or any combination thereof.

Any method which is described and illustrated herein is not limited to the exact sequence of acts described, nor is it necessarily limited to the practice of all of the acts set forth. Other sequences of events or acts, or less than all of the events, or simultaneous occurrence of the events, may be utilized in practicing the method(s) in question.

A. Noninvasive System

1. Monitor Structure

FIG. 1 depicts a noninvasive optical detection system (hereinafter "noninvasive system") 10 in a presently preferred configuration. The depicted noninvasive system 10 is particularly suited for noninvasively detecting the concentration of an analyte in a material sample S, by observing the infrared energy emitted by the sample, as will be discussed in further detail below.

As used herein, the term "noninvasive" is a broad term and is used in its ordinary sense and refers, without limitation, to analyte detection devices and methods which have the capability to determine the concentration of an analyte in in-vivo tissue samples or bodily fluids. It should be understood, however, that the noninvasive system 10 disclosed herein is not limited to noninvasive use, as the noninvasive system 10 may be employed to analyze an in-vitro fluid or tissue sample which has been obtained invasively or noninvasively. As used herein, the term "invasive" (or, alternatively, "traditional") is a broad term and is used in its ordinary sense and refers, without limitation, to analyte detection methods which involve the removal of fluid samples through the skin. As used herein, the term "material sample" is a broad term and is used in its ordinary sense and refers, without limitation, to any collection of material which is suitable for analysis by the noninvasive system 10. For example, the material sample S may comprise a tissue sample, such as a human forearm, placed against the noninvasive system 10. The material sample S may also comprise a volume of a bodily fluid, such as whole blood, blood component(s), interstitial fluid or intercellular fluid obtained invasively, or saliva or urine obtained noninvasively, or any collection of organic or inorganic material. As used herein, the term "analyte" is a broad term and is used in its ordinary sense and refers, without limitation, to any chemical species the presence or concentration of which is sought in the material sample S by the noninvasive system 10. For example, the analyte(s) which may be detected by the noninvasive system 10 include but not are limited to glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, electrolytes, sodium, potassium, chloride, bicarbonate, and hormones. As used herein to describe measurement techniques, the term "continuous" is a broad term and is used in its ordinary sense and refers, without limitation, to the taking of discrete measurements more frequently than about once every 10 minutes, and/or the taking of a stream or series of measurements or other data over any suitable time interval, for example, over an interval of one to several seconds, minutes, hours, days, or longer. As used herein to describe measurement techniques, the term "intermittent" is a broad term and is used in its ordinary sense and refers, without limitation, to the taking of measurements less frequently than about once every 10 minutes.

The noninvasive system 10 preferably comprises a window assembly 12, although in some embodiments the window assembly 12 may be omitted. One function of the window assembly 12 is to permit infrared energy E to enter the noninvasive system 10 from the sample S when it is placed against an upper surface 12a of the window assembly 12. The window assembly 12 includes a heater layer (see discussion below) which is employed to heat the material sample S and stimulate emission of infrared energy therefrom. A cooling system 14, preferably comprising a Peltier-type thermoelectric device, is in thermally conductive relation to the window assembly 12 so that the temperature of the window assembly 12 and the material sample S can be manipulated in accordance with a detection methodology discussed in greater detail below. The cooling system 14 includes a cold surface 14a which is in thermally conductive relation to a cold reservoir 16 and the window assembly 12, and a hot surface 14b which is in thermally conductive relation to a heat sink 18.

As the infrared energy E enters the noninvasive system 10, it first passes through the window assembly 12, then through an optical mixer 20, and then through a collimator 22. The optical mixer 20 preferably comprises a light pipe having highly reflective inner surfaces which randomize the directionality of the infrared energy E as it passes therethrough and reflects against the mixer walls. The collimator 22 also comprises a light pipe having highly-reflective inner walls, but the walls diverge as they extend away from the mixer 20. The divergent walls cause the infrared energy E to tend to straighten as it advances toward the wider end of the collimator 22, due to the angle of incidence of the infrared energy when reflecting against the collimator walls.

From the collimator 22 the infrared energy E passes through an array of filters 24, each of which allows only a selected wavelength or band of wavelengths to pass therethrough. These wavelengths/bands are selected to highlight or isolate the absorptive effects of the analyte of interest in the detection methodology discussed in greater detail below. Each filter 24 is preferably in optical communication with a concentrator 26 and an infrared detector 28. The concentrators 26 have highly reflective, converging inner walls which concentrate the infrared energy as it advances toward the detectors 28, increasing the density of the energy incident upon the detectors 28.

The detectors 28 are in electrical communication with a control system 30 which receives electrical signals from the detectors 28 and computes the concentration of the analyte in the sample S. The control system 30 is also in electrical communication with the window 12 and cooling system 14, so as to monitor the temperature of the window 12 and/or cooling system 14 and control the delivery of electrical power to the window 12 and cooling system 14.

a. Window Assembly

Figure 2:
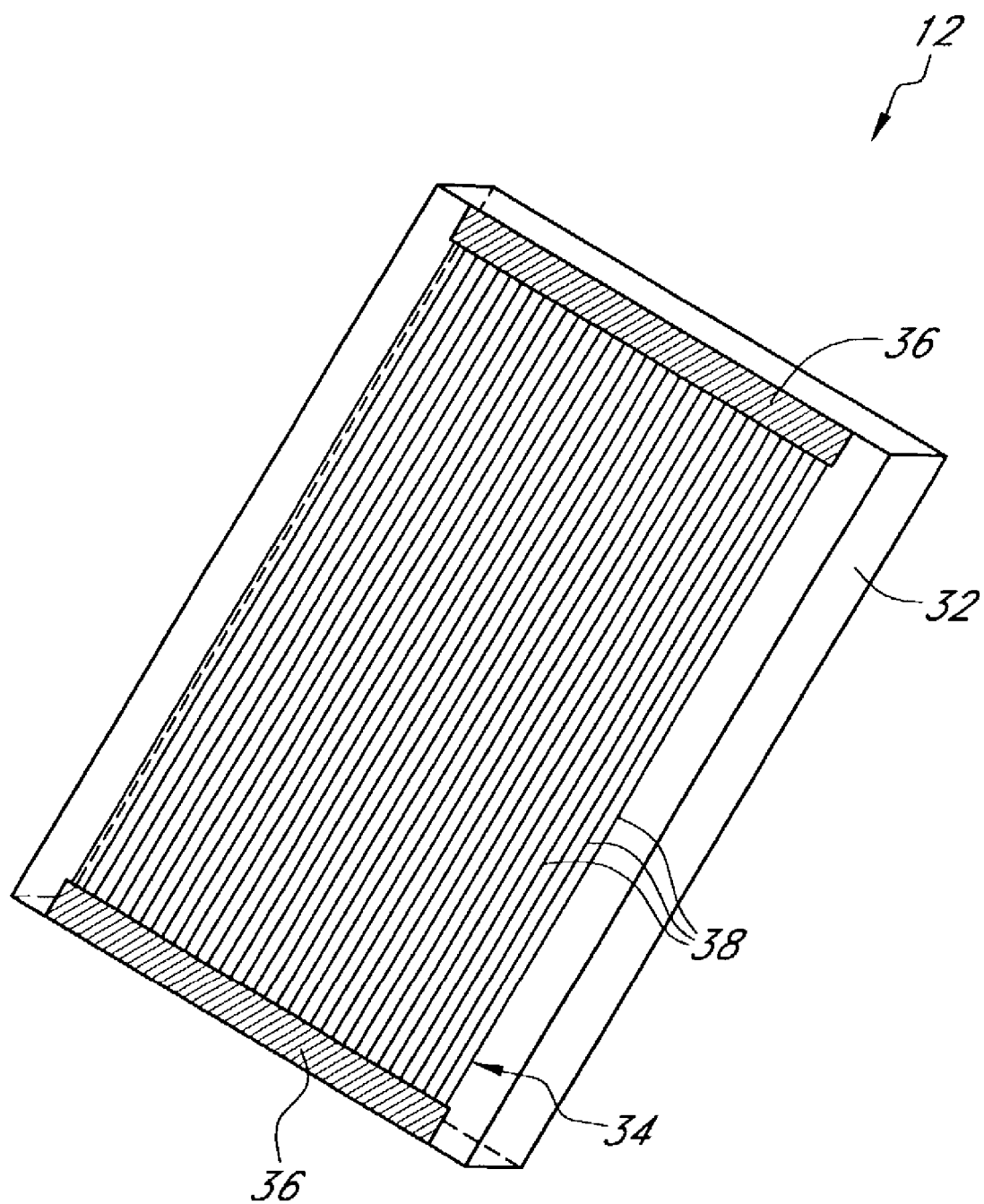
FIG. 2 is a perspective view of a window assembly for use with the noninvasive detection system.

A preferred configuration of the window assembly 12 is shown in perspective, as viewed from its underside (in other words, the side of the window assembly 12 opposite the sample S), in FIG. 2. The window assembly 12 generally comprises a main layer 32 formed of a highly infrared-transmissive material and a heater layer 34 affixed to the underside of the main layer 32. The main layer 32 is preferably formed from diamond, most preferably from chemical-vapor-deposited ("CVD") diamond, with a preferred thickness of about 0.25 millimeters. In other embodiments alternative materials which are highly infrared-transmissive, such as silicon or germanium, may be used in forming the main layer 32.

The heater layer 34 preferably comprises bus bars 36 located at opposing ends of an array of heater elements 38. The bus bars 36 are in electrical communication with the elements 38 so that, upon connection of the bus bars 36 to a suitable electrical power source (not shown) a current may be passed through the elements 38 to generate heat in the window assembly 12. The heater layer 34 may also include one or more temperature sensors (not shown), such as thermistors or resistance temperature devices (RTDs), to measure the temperature of the window assembly 12 and provide temperature feedback to the control system 30 (see FIG. 1).

Still referring to FIG. 2, the heater layer 34 preferably comprises a first adhesion layer of gold or platinum (hereinafter referred to as the "gold" layer) deposited over an alloy layer which is applied to the main layer 32. The alloy layer comprises a material suitable for implementation of the heater layer 34, such as, by way of example, 10/90 titanium/tungsten, titanium/platinum, nickel/chromium, or other similar material. The gold layer preferably has a thickness of about 4000 Å, and the alloy layer preferably has a thickness ranging between about 300 Å and about 500 Å. The gold layer and/or the alloy layer may be deposited onto the main layer 32 by chemical deposition including, but not necessarily limited to, vapor deposition, liquid deposition, plating, laminating, casting, sintering, or other forming or deposition methodologies well known to those or ordinary skill in the art. If desired, the heater layer 34 may be covered with an electrically insulating coating which also enhances adhesion to the main layer 32. One preferred coating material is aluminum oxide. Other acceptable materials include, but are not limited to, titanium dioxide or zinc selenide.

The heater layer 34 may incorporate a variable pitch distance between centerlines of adjacent heater elements 38 to maintain a constant power density, and promote a uniform temperature, across the entire layer 34. Where a constant pitch distance is employed, the preferred distance is at least about 50–100 microns. Although the heater elements 38 generally have a preferred width of about 25 microns, their width may also be varied as needed for the same reasons stated above.

Alternative structures suitable for use as the heater layer 34 include, but are not limited to, thermoelectric heaters, radiofrequency (RF) heaters, infrared radiation heaters, optical heaters, heat exchangers, electrical resistance heating grids, wire bridge heating grids, or laser heaters. Whichever type of heater layer is employed, it is preferred that the heater layer obscures about 10% or less of the window assembly 12.

In a preferred embodiment, the window assembly 12 comprises substantially only the main layer 32 and the heater layer 34. Thus, when installed in an optical detection system such as the noninvasive system 10 shown in FIG. 1, the window assembly 12 will facilitate a minimally obstructed optical path between a (preferably flat) upper surface 12a of the window assembly 12 and the infrared detectors 28 of the noninvasive system 10. The optical path 32 in the preferred noninvasive system 10 proceeds only through the main layer 32 and heater layer 34 of the window assembly 12 (including any antireflective, index-matching, electrical insulating or protective coatings applied thereto or placed therein), through the optical mixer 20 and collimator 22 and to the detectors 28.

Figure 2A:
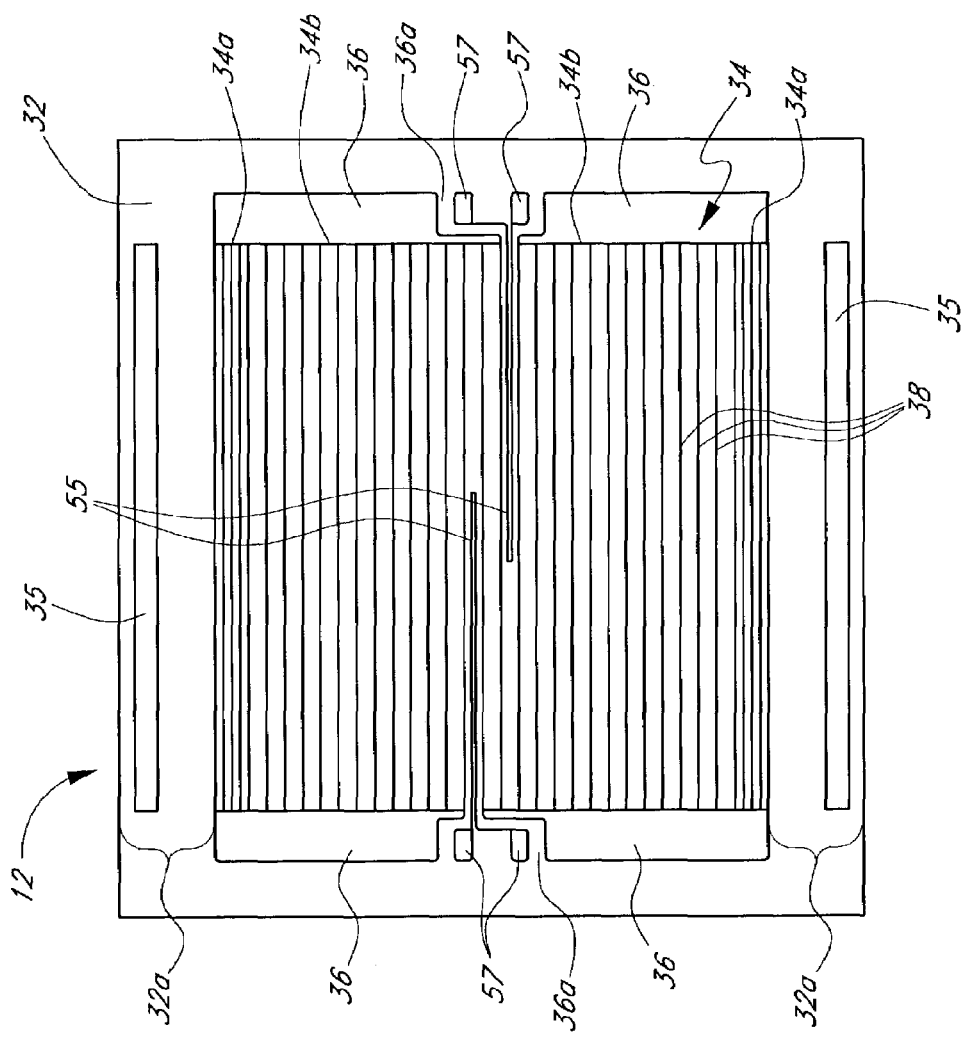
FIG. 2A is a plan view of another embodiment of a window assembly for use with the noninvasive detection system.

FIG. 2A shows another embodiment of the window assembly 12, that may be used in place of the window assembly 12 depicted in FIG. 2. The window assembly 12 shown in FIG. 2A may be similar to that shown in FIG. 2, except as described below. In the embodiment of FIG. 2A the main layer 32 has a preferred thickness of up to about 0.012" and more preferably about 0.010" or less. The heater layer 34 may also include one or more resistance temperature devices (RTD's) 55 to measure the temperature of the window assembly 12 and provide temperature feedback to a control system 30. The RTDs 55 terminate in RTD connection pads 57.

In the embodiment of FIG. 2A, the heater elements 38 are typically provided with a width of about 25 microns. The pitch distance separating centerlines of adjacent heater elements 38 may be reduced, and/or the width of the heater elements 38 may be increased, in the regions of the window assembly 12 near the point(s) of contact with the thermal diffuser 410 (see FIGS. 6B–6D and discussion below). This arrangement advantageously promotes an isothermal temperature profile at the upper surface of the main layer 32 despite thermal contact with the thermal diffuser.

The embodiment shown in FIG. 2A includes a plurality of heater elements 38 of substantially equal width which are variably spaced across the width of the main layer 32. In the embodiment of FIG. 2A, the centerlines of the heater elements 38 are spaced at a first pitch distance of about 0.0070" at peripheral portions 34a of the heater layer 34, and at a second pitch distance of about 0.015" at a central portion 34b of the main layer 32. The heater elements 38 closest to the center are preferably sufficiently spaced to allow the RTDs 55 to extend therebetween. In the embodiment of FIG. 2A, the main layer 32 includes peripheral regions 32a which extend about 0.053" from the outermost heater element on each side of the heater layer 34 to the adjacent edge of the main layer 32. As shown, the bus bars 36 are preferably configured and segmented to allow space for the RTDs 55 and the RTD connection pads 57, in intermediate gaps 36a. The RTDs 55 preferably extend into the array of heater elements 38 by distance that is slightly longer than half of the length of an individual heater element 38. In alternative embodiments, the RTDs 55 may be located at the edges of the main layer 32, or at other locations as desired for a particular noninvasive system.

With continued reference to FIG. 2A, the peripheral regions of the main layer 32 may include metallized edge portions 35 for facilitating connection to the diffuser 410 (discussed below in connection with FIGS. 6B–6D). The metallized edge portions 35 may be formed by the same or similar processes used in forming the heater elements 38 and RTDs 55. In the embodiment of FIG. 2A, the edge portions 35 are typically between about 0.040" and about 0.060" wide by about 0.450" and about 0.650" long, and in one embodiment, they are about 0.050" by about 0.550". Other dimensions may be appropriately used so long as the window assembly 12 may be joined in thermal communication with the diffuser 410 as needed.

In the embodiment shown in FIG. 2A, the main layer 32 is about 0.690" long by about 0.571" wide, and the heater layer (excluding the metallized edge portions 35) is about 0.640" long by about 0.465" wide. The main layer 32 is about 0.010"–0.012" thick, and is advantageously thinner than about 0.010" where possible. Each heater element 38 is about 0.570" long, and each peripheral region 34a is about 0.280" wide. These dimensions are merely exemplary; of course, other dimensions may be used as desired.

Figure 3:
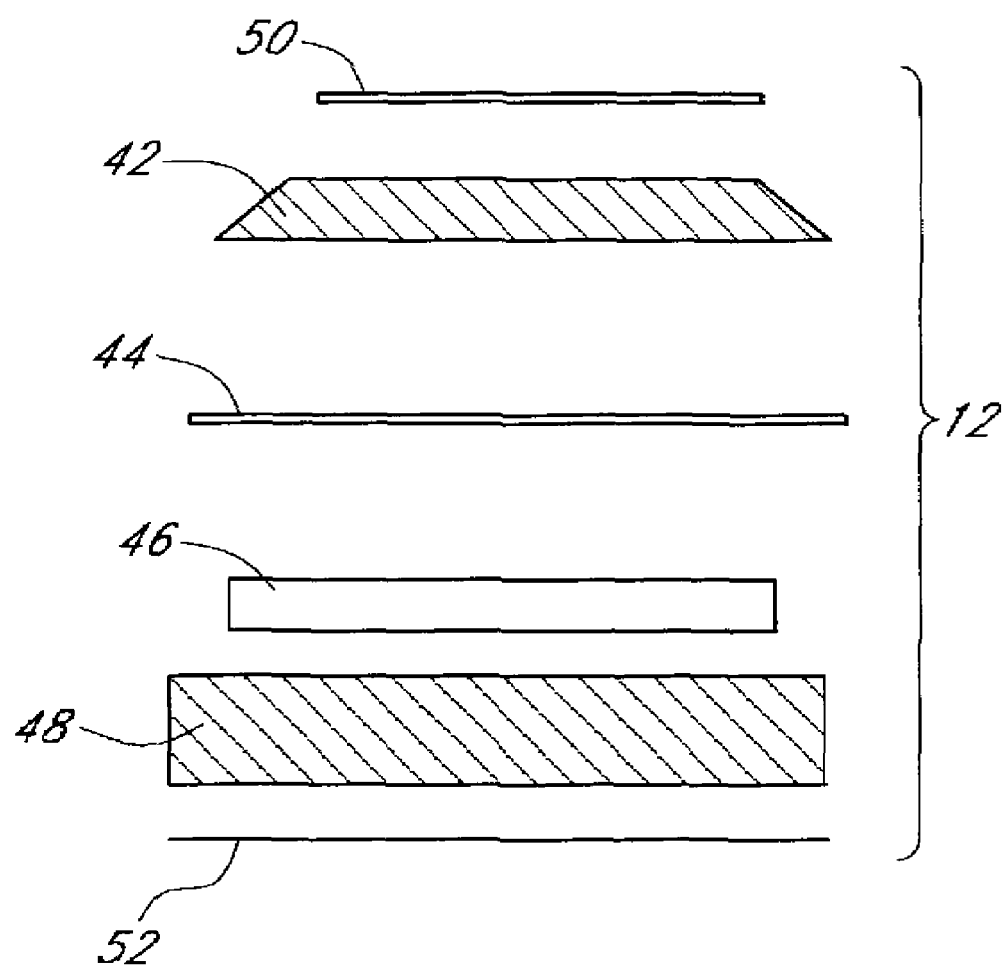
FIG. 3 is an exploded schematic view of another embodiment of a window assembly for use with the noninvasive detection system.

FIG. 3 depicts an exploded side view of an alternative configuration for the window assembly 12, which may be used in place of the configuration shown in FIG. 2. The window assembly 12 depicted in FIG. 3 includes near its upper surface (the surface intended for contact with the sample S) a highly infrared-transmissive, thermally conductive spreader layer 42. Underlying the spreader layer 42 is a heater layer 44. A thin electrically insulating layer (not shown), such as layer of aluminum oxide, titanium dioxide or zinc selenide, may be disposed between the heater layer 44 and the spreader layer 42. (An aluminum oxide layer also increases adhesion of the heater layer 44 to the spreader layer 42.) Adjacent to the heater layer 44 is a thermal insulating and impedance matching layer 46. Adjacent to the thermal insulating layer 46 is a thermally conductive inner layer 48. The spreader layer 42 is coated on its top surface with a thin layer of protective coating 50. The bottom surface of the inner layer 48 is coated with a thin overcoat layer 52. Preferably, the protective coating 50 and the overcoat layer 52 have antireflective properties.

The spreader layer 42 is preferably formed of a highly infrared-transmissive material having a high thermal conductivity sufficient to facilitate heat transfer from the heater layer 44 uniformly into the material sample S when it is placed against the window assembly 12. Other effective materials include, but are not limited to, CVD diamond, diamondlike carbon, gallium arsenide, germanium, and other infrared-transmissive materials having sufficiently high thermal conductivity. Preferred dimensions for the spreader layer 42 are about one inch in diameter and about 0.010 inch thick. As shown in FIG. 3, a preferred embodiment of the spreader layer 42 incorporates a beveled edge. Although not required, an approximate 45-degree bevel is preferred.

The protective layer 50 is intended to protect the top surface of the spreader layer 42 from damage. Ideally, the protective layer is highly infrared-transmissive and highly resistant to mechanical damage, such as scratching or abrasion. It is also preferred that the protective layer 50 and the overcoat layer 52 have high thermal conductivity and anti-reflective and/or index-matching properties. A satisfactory material for use as the protective layer 50 and the overcoat layer 52 is the multi-layer Broad Band Anti-Reflective Coating produced by Deposition Research Laboratories, Inc. of St. Charles, Miss. Diamondlike carbon coatings are also suitable.

Except as noted below, the heater layer 44 is generally similar to the heater layer 34 employed in the window assembly shown in FIG. 2. Alternatively, the heater layer 44 may comprise a doped infrared-transmissive material, such as a doped silicon layer, with regions of higher and lower resistivity. The heater layer 44 preferably has a resistance of about 2 ohms and has a preferred thickness of about 1,500 angstroms. A preferred material for forming the heater layer 44 is a gold alloy, but other acceptable materials include, but are not limited to, platinum, titanium, tungsten, copper, and nickel.

The thermal insulating layer 46 prevents the dissipation of heat from the heater element 44 while allowing the cooling system 14 to effectively cool the material sample S (see FIG. 1). This layer 46 comprises a material having thermally insulative (e.g., lower thermal conductivity than the spreader layer 42) and infrared transmissive qualities. A preferred material is a germanium-arsenic-selenium compound of the calcogenide glass family known as AMTIR-1 produced by Amorphous Materials, Inc. of Garland, Texas. The pictured embodiment has a diameter of about 0.85 inches and a preferred thickness in the range of about 0.005 to about 0.010 inches. As heat generated by the heater layer 44 passes through the spreader layer 42 into the material sample S, the thermal insulating layer 46 insulates this heat.

The inner layer 48 is formed of thermally conductive material, preferably crystalline silicon formed using a conventional floatzone crystal growth method. The purpose of the inner layer 48 is to serve as a cold-conducting mechanical base for the entire layered window assembly.

The overall optical transmission of the window assembly 12 shown in FIG. 3 is preferably at least 70%. The window assembly 12 of FIG. 3 is preferably held together and secured to the noninvasive system 10 by a holding bracket (not shown). The bracket is preferably formed of a glass-filled plastic, for example Ultem 2300, manufactured by General Electric. Ultem 2300 has low thermal conductivity which prevents heat transfer from the layered window assembly 12.

b. Cooling System

The cooling system 14 (see FIG. 1) preferably comprises a Peltier-type thermoelectric device. Thus, the application of an electrical current to the preferred cooling system 14 causes the cold surface 14a to cool and causes the opposing hot surface 14b to heat up. The cooling system 14 cools the window assembly 12 via the situation of the window assembly 12 in thermally conductive relation to the cold surface 14a of the cooling system 14. It is contemplated that the cooling system 14, the heater layer 34, or both, can be operated to induce a desired time-varying temperature in the window assembly 12 to create an oscillating thermal gradient in the sample S, in accordance with various analyte-detection methodologies discussed herein.

Preferably, the cold reservoir 16 is positioned between the cooling system 14 and the window assembly 12, and functions as a thermal conductor between the system 14 and the window assembly 12. The cold reservoir 16 is formed from a suitable thermally conductive material, preferably brass. Alternatively, the window assembly 12 can be situated in direct contact with the cold surface 14a of the cooling system 14.

In alternative embodiments, the cooling system 14 may comprise a heat exchanger through which a coolant, such as air, nitrogen or chilled water, is pumped, or a passive conduction cooler such as a heat sink. As a further alternative, a gas coolant such as nitrogen may be circulated through the interior of the noninvasive system 10 so as to contact the underside of the window assembly 12 (see FIG. 1) and conduct heat therefrom.

Figure 4:
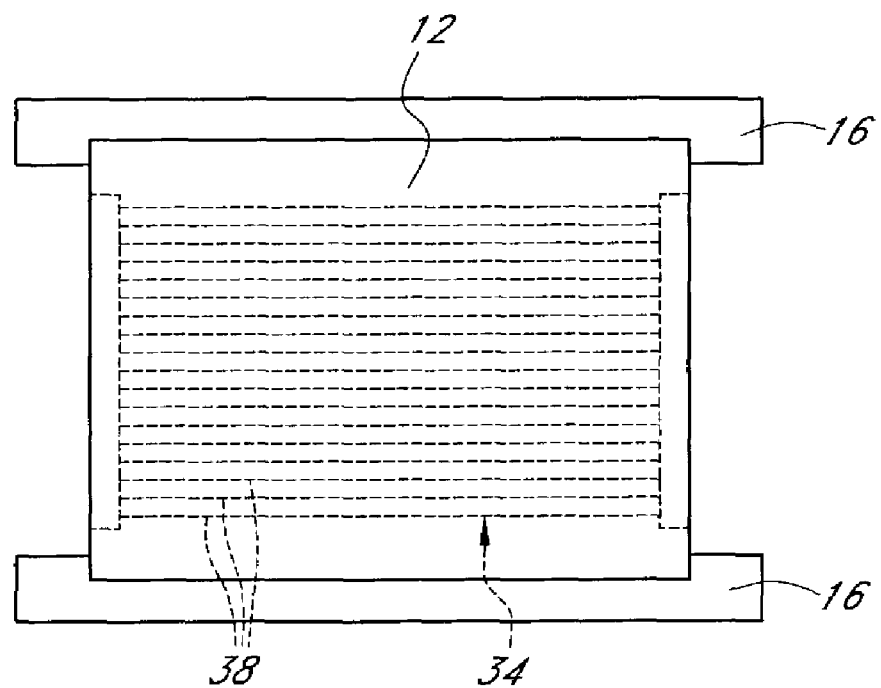
FIG. 4 is a plan view of the window assembly connected to a cooling system.
Figure 5:
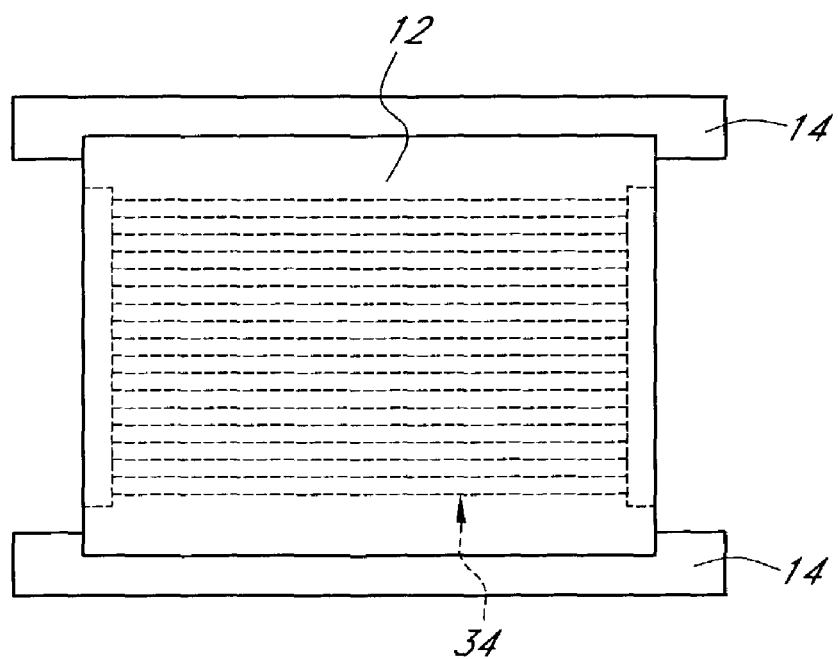
FIG. 5 is a plan view of the window assembly connected to a cold reservoir.

FIG. 4 is a top schematic view of a preferred arrangement of the window assembly 12 (of the types shown in FIG. 2 or 2A) and the cold reservoir 16, and FIG. 5 is a top schematic view of an alternative arrangement in which the window assembly 12 directly contacts the cooling system 14. The cold reservoir 16/cooling system 14 preferably contacts the underside of the window assembly 12 along opposing edges thereof, on either side of the heater layer 34. With thermal conductivity thus established between the window assembly 12 and the cooling system 14, the window assembly can be cooled as needed during operation of the noninvasive system 10. In order to promote a substantially uniform or isothermal temperature profile over the upper surface of the window assembly 12, the pitch distance between centerlines of adjacent heater elements 38 may be made smaller (thereby increasing the density of heater elements 38) near the region(s) of contact between the window assembly 12 and the cold reservoir 16/cooling system 14. As a supplement or alternative, the heater elements 38 themselves may be made wider near these regions of contact. As used herein, "isothermal" is a broad term and is used in its ordinary sense and refers, without limitation, to a condition in which, at a given point in time, the temperature of the window assembly 12 or other structure is substantially uniform across a surface intended for placement in thermally conductive relation to the material sample S. Thus, although the temperature of the structure or surface may fluctuate over time, at any given point in time the structure or surface may nonetheless be isothermal.

Figure 6:
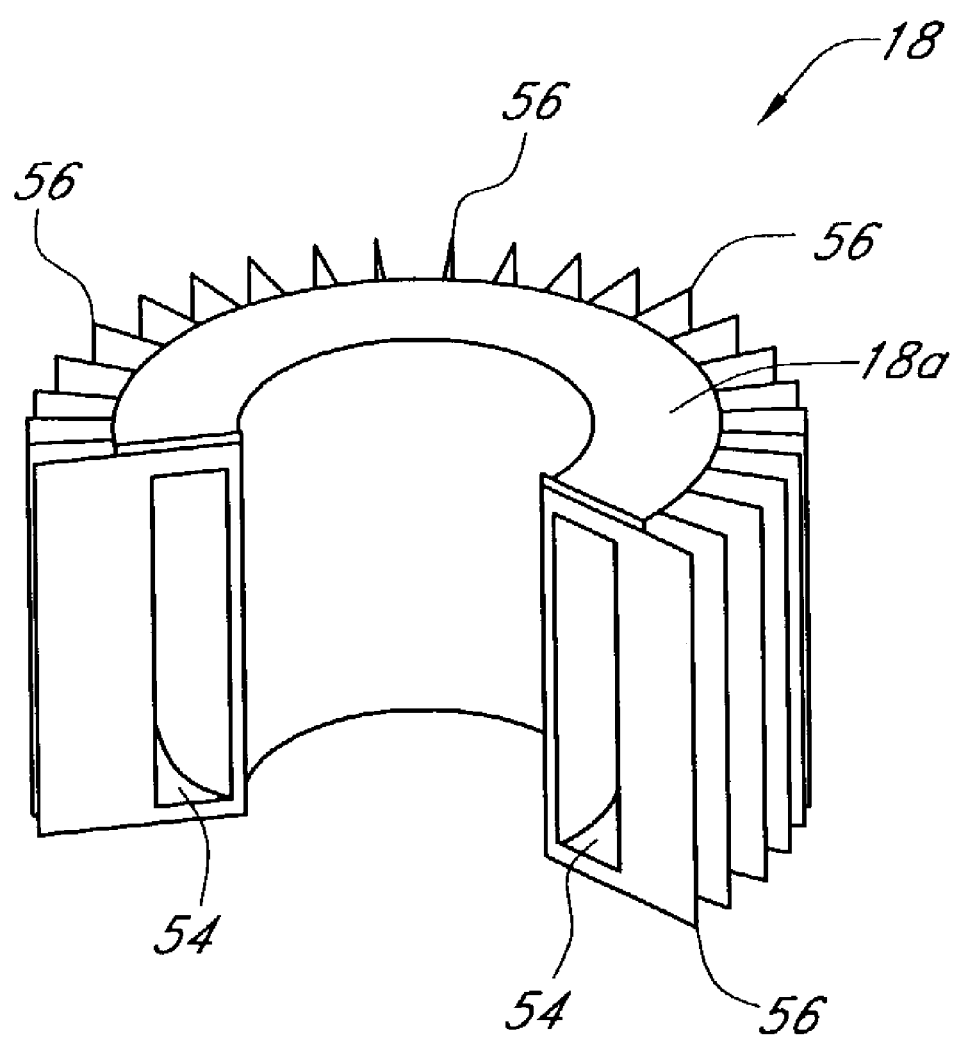
FIG. 6 is a cutaway view of a heat sink for use with the noninvasive detection system.

The heat sink 18 drains waste heat from the hot surface 14b of the cooling system 16 and stabilizes the operational temperature of the noninvasive system 10. The preferred heat sink 18 (see FIG. 6) comprises a hollow structure formed from brass or any other suitable material having a relatively high specific heat and high heat conductivity. The heat sink 18 has a conduction surface 18a which, when the heat sink 18 is installed in the noninvasive system 18, is in thermally conductive relation to the hot surface 14b of the cooling system 14 (see FIG. 1). A cavity 54 is formed in the heat sink 18 and preferably contains a phase-change material (not shown) to increase the capacity of the sink 18. A preferred phase change material is a hydrated salt, such as calciumchloride hexahydrate, available under the name TH29 from PCM Thermal Solutions, Inc., of Naperville, Ill. Alternatively, the cavity 54 may be omitted to create a heat sink 18 comprising a solid, unitary mass. The heat sink 18 also forms a number of fins 56 to further increase the conduction of heat from the sink 18 to surrounding air.

Alternatively, the heat sink 18 may be formed integrally with the optical mixer 20 and/or the collimator 22 as a unitary mass of rigid, heat-conductive material such as brass or aluminum. In such a heat sink, the mixer 20 and/or collimator 22 extend axially through the heat sink 18, and the heat sink defines the inner walls of the mixer 20 and/or collimator 22. These inner walls are coated and/or polished to have appropriate reflectivity and nonabsorbance in infrared wavelengths as will be further described below. Where such a unitary heat sink-mixer-collimator is employed, it is desirable to thermally insulate the detector array from the heat sink.

It should be understood that any suitable structure may be employed to heat and/or cool the material sample S, instead of or in addition to the window assembly 12/cooling system 14 disclosed above, so long a proper degree of cycled heating and/or cooling are imparted to the material sample S. In addition other forms of energy, such as but not limited to light, radiation, chemically induced heat, friction and vibration, may be employed to heat the material sample S. It will be further appreciated that heating of the sample can achieved by any suitable method, such as convection, conduction, radiation, etc.

c. Window Mounting System

Figure 6A:
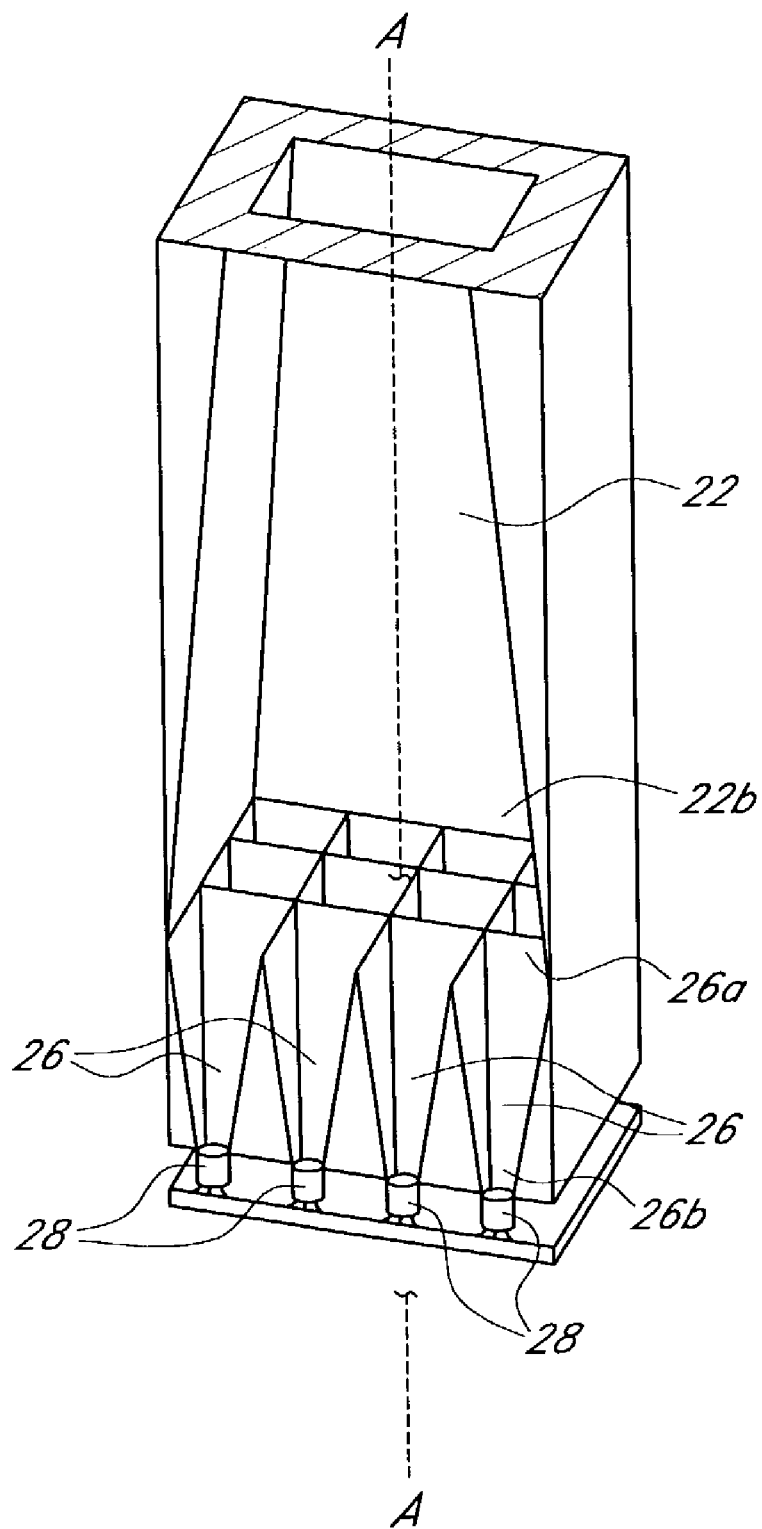
FIG. 6A is a cutaway perspective view of a lower portion of the noninvasive detection system of FIG. 1.
Figure 6B:
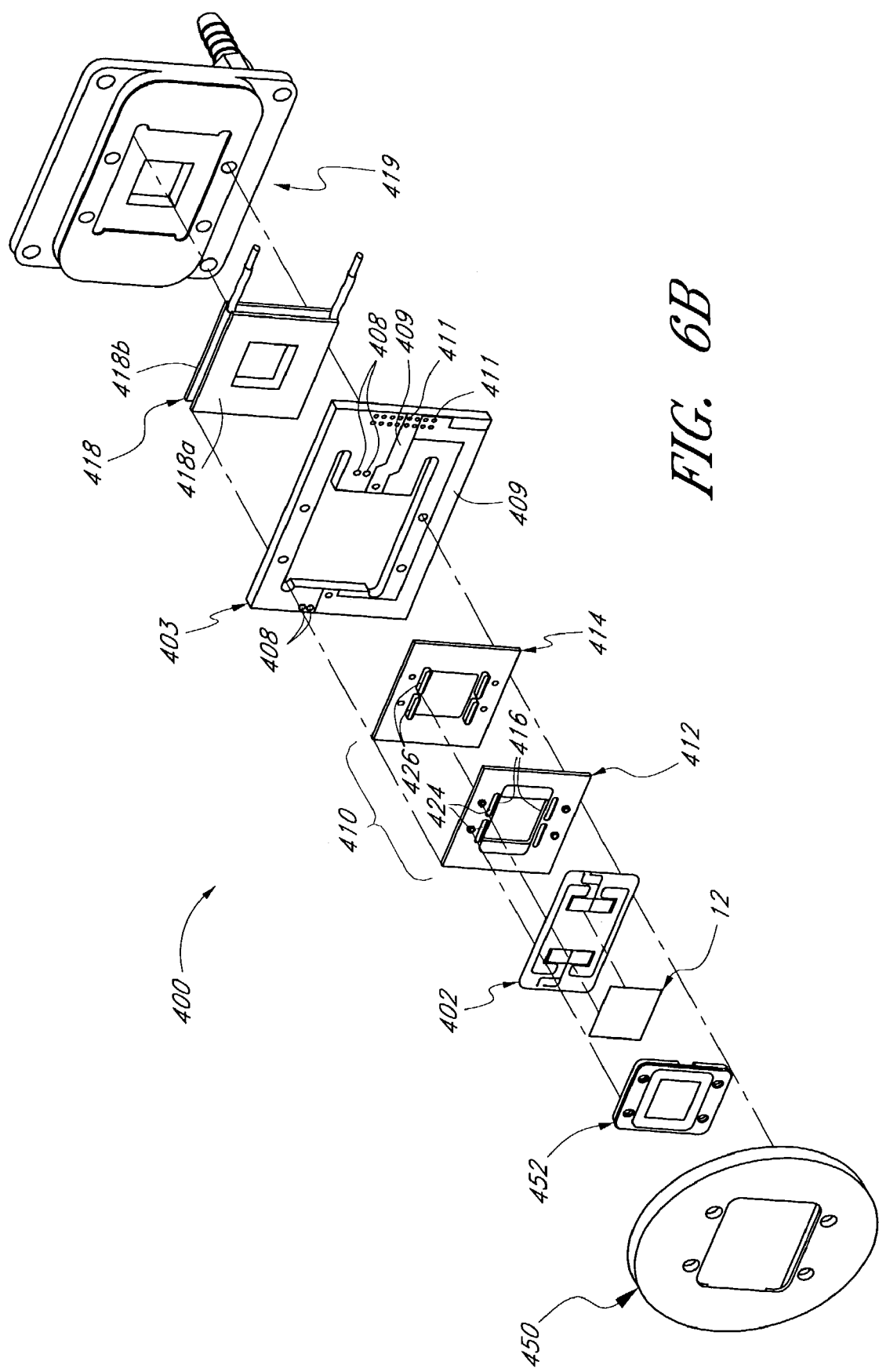
FIG. 6B is an exploded perspective view of a window mounting system for use with the noninvasive optical detection system.

FIG. 6B illustrates an exploded view of a window mounting system 400 which, in one embodiment, is employed as part of the noninvasive system 10 disclosed above. Where employed in connection with the noninvasive system 10, the window mounting system 400 supplements or, where appropriate, replaces any of the window assembly 12, cooling system 14, cold reservoir 16 and heat sink 18 shown in FIG. 1. In one embodiment, the window mounting system 400 is employed in conjunction with the window assembly 12 depicted in FIG. 2A; in alternative embodiments, the window assemblies shown in FIGS. 2 and 3 and described above may also be used in conjunction with the window mounting system 400 illustrated in FIG. 6B.

In the window mounting system 400, the window assembly 12 is physically and electrically connected (typically by soldering) to a first printed circuit board ("first PCB") 402. The window assembly 12 is also in thermally conductive relation (typically by contact) to a thermal diffuser 410. The window assembly may also be fixed to the diffuser 410 by soldering.

The thermal diffuser 410 generally comprises a heat spreader layer 412 which, as mentioned, preferably contacts the window assembly 12, and a conductive layer 414 which is typically soldered to the heat spreader layer 412. The conductive layer 414 may then be placed in direct contact with a cold side 418a of a thermoelectric cooler (TEC) 418 or other cooling device. The TEC 418, which in one embodiment comprises a 25 W TEC manufactured by MELCOR, is in electrical communication with a second PCB 403, which includes TEC power leads 409 and TEC power terminals 411 for connection of the TEC 418 to an appropriate power source (not shown). The second PCB 403 also includes contacts 408 for connection with RTD terminals 407 (see FIG. 6C) of the first PCB 402. A heat sink 419, which may take the form of the illustrated water jacket, the heat sink 18 shown in FIG. 6, any other heat sink structures mentioned herein, or any other appropriate device, is in thermal communication with a hot side 418b of the TEC 418 (or other cooling device), in order to remove any excess heat created by the TEC 418.

Figure 6C:
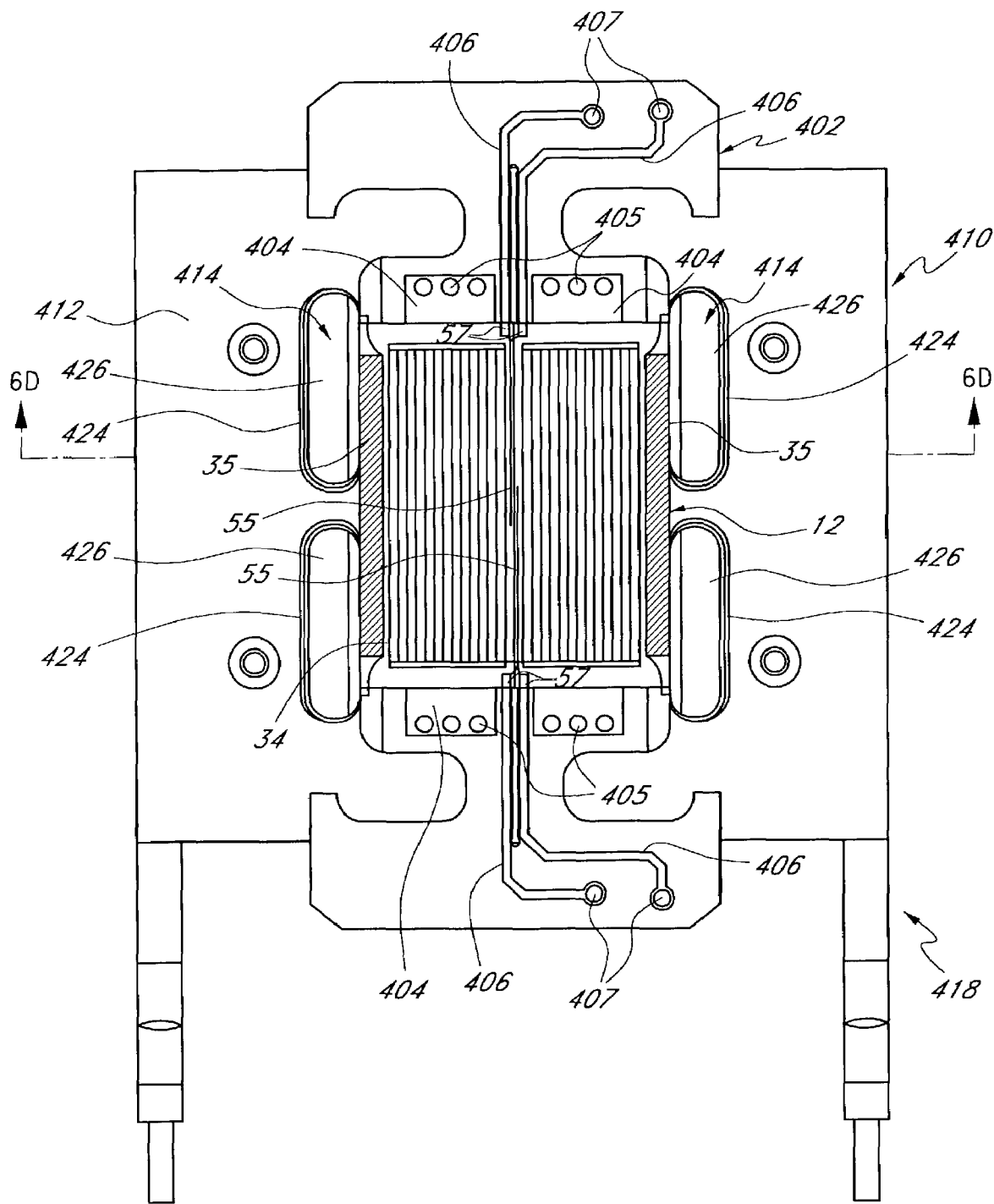
FIG. 6C is a partial plan view of the window mounting system of FIG. 6B.

FIG. 6C illustrates a plan view of the interconnection of the window assembly 12, the first PCB 402, the diffuser 410 and the thermoelectric cooler 418. The first PCB includes RTD bonding leads 406 and heater bonding pads 404 which permit attachment of the RTDs 55 and bus bars 36, respectively, of the window assembly 12 to the first PCB 402 via soldering or other conventional techniques. Electrical communication is thus established between the heater elements 38 of the heater layer 34, and heater terminals 405 formed in the heater bonding pads 404. Similarly, electrical communication is established between the RTDs 55 and RTD terminals 407 formed at the ends of the RTD bonding leads 406. Electrical connections can be established with the heater elements 38 and the RTDs 55 via simple connection to the terminals 405, 407 of the first PCB 402.

With further reference to FIGS. 2A and 6B–6C, the heat spreader layer 412 of the thermal diffuser 410 contacts the underside of the main layer 32 of the window assembly 12 via a pair of rails 416. The rails 416 may contact the main layer 32 at the metallized edge portions 35, or at any other appropriate location. The physical and thermal connection between the rails 416 and the window main layer 32 may be achieved by soldering, as indicated above. Alternatively, the connection may be achieved by an adhesive such as epoxy, or any other appropriate method. The material chosen for the window main layer 32 is preferably sufficiently thermally conductive that heat may be quickly removed from the main layer 32 through the rails 416, the diffuser 410, and the TEC 128.

Figure 6D:
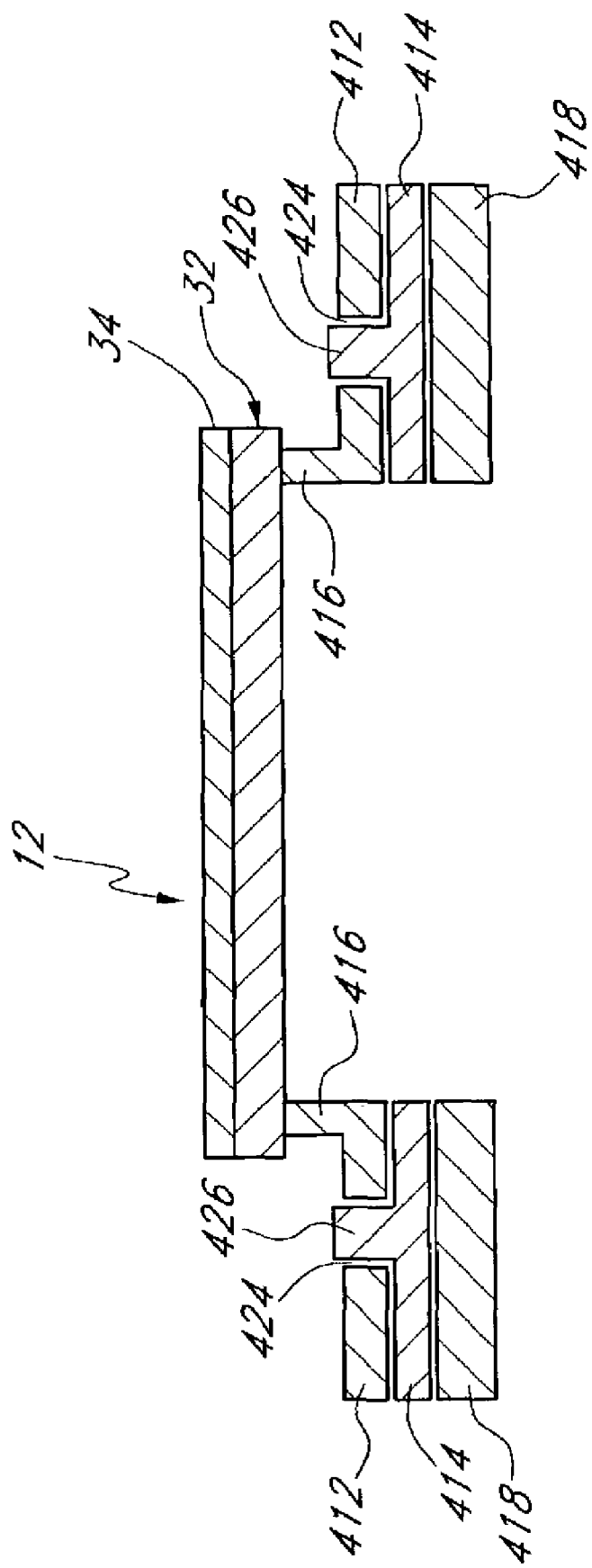
FIG. 6D is a sectional view of the window mounting system of FIG. 6C.

FIG. 6D shows a cross-sectional view of the assembly of FIG. 6C through line 22—22. As can be seen in FIG. 6D, the window assembly 12 contacts the rails 416 of the heat spreader layer 412. The conductive layer 414 underlies the spreader layer 412 and may comprise protrusions 426 configured to extend through openings 424 formed in the spreader layer 412. The openings 424 and protrusions 426 are sized to leave sufficient expansion space therebetween, to allow expansion and contraction of the conductive layer 414 without interference with, or causing deformation of, the window assembly 12 or the heat spreader layer 412. Moreover, the protrusions 426 and openings 424 coact to prevent displacement of the spreader layer 412 with respect to the conductive layer 414 as the conductive layer 414 expands and contracts.

The thermal diffuser 410 provides a thermal impedance between the TEC 418 and the window assembly 12, which impedance is selected to drain heat from the window assembly at a rate proportional to the power output of the heater layer 34. In this way, the temperature of the main layer 32 can be rapidly cycled between a "hot" and a "cold" temperatures, thereby allowing a time-varying thermal gradient to be induced in a sample S placed against the window assembly 12.

The heat spreader layer 412 is preferably made of a material which has substantially the same coefficient of thermal expansion as the material used to form the window assembly main layer 32, within the expected operating temperature range. Preferably, both the material used to form the main layer 32 and the material used to form the heat spreader layer 412 have substantially the same, extremely low, coefficient of thermal expansion. For this reason, CVD diamond is preferred for the main layer 32 (as mentioned above); with a CVD diamond main layer 32 the preferred material for the heat spreader layer 412 is Invar. Invar advantageously has an extremely low coefficient of thermal expansion and a relatively high thermal conductivity. Because Invar is a metal, the main layer 32 and the heat spreader layer 412 can be thermally bonded to one another with little difficulty. Alternatively, other materials may be used for the heat spreader layer 412; for example, any of a number of glass and ceramic materials with low coefficients of thermal expansion may be employed.

The conductive layer 414 of the thermal diffuser 410 is typically a highly thermally conductive material such as copper (or, alternatively, other metals or non-metals exhibiting comparable thermal conductivities). The conductive layer 414 is typically soldered or otherwise bonded to the underside of the heat spreader layer 412.

In the illustrated embodiment, the heat spreader layer 412 may be constructed according to the following dimensions, which are to be understood as exemplary; accordingly the dimensions may be varied as desired. The heat spreader layer 412 has an overall length and width of about 1.170", with a central opening of about 0.590" long by 0.470" wide. Generally, the heat spreader layer 412 is about 0.030" thick; however, the rails 416 extend a further 0.045" above the basic thickness of the heat spreader layer 412. Each rail 416 has an overall length of about 0.710"; over the central 0.525" of this length each rail 416 is about 0.053" wide. On either side of the central width each rail 416 tapers, at a radius of about 0.6", down to a width of about 0.023". Each opening 424 is about 0.360" long by about 0.085" wide, with corners rounded at a radius of about 0.033".

In the illustrated embodiment, conductive layer 414 may be constructed according to the following dimensions, which are to be understood as exemplary; accordingly the dimensions may be varied as desired. The conductive layer 414 has an overall length and width of about 1.170", with a central opening of about 0.590" long by 0.470" wide. Generally, the conductive layer 412 is about 0.035" thick; however, the protrusions 426 extend a further 0.075"–0.085" above the basic thickness of the conductive layer 414. Each protrusion 426 is about 0.343" long by about 0.076" wide, with corners rounded at a radius of about 0.035".

As shown in FIG. 6B, first and second clamping plates 450 and 452 may be used to clamp the portions of the window mounting system 400 to one another. For example, the second clamping plate 452 is configured to clamp the window assembly 12 and the first PCB 402 to the diffuser 410 with screws or other fasteners extending through the openings shown in the second clamping plate 452, the heat spreader layer 412 and the conductive layer 414. Similarly, the first clamping plate 450 is configured overlie the second clamping plate 452 and clamp the rest of the window mounting system 400 to the heat sink 419, thus sandwiching the second clamping plate 452, the window assembly 12, the first PCB 402, the diffuser 410, the second PCB 403, and the TEC 418 therebetween. The first clamping plate 450 prevents undesired contact between the sample S and any portion of the window mounting system 400, other than the window assembly 12 itself. Other mounting plates and mechanisms may also be used as desired.

d. Optics

As shown in FIG. 1, the optical mixer 20 comprises a light pipe with an inner surface coating which is highly reflective and minimally absorptive in infrared wavelengths, preferably a polished gold coating, although other suitable coatings may be used where other wavelengths of electromagnetic radiation are employed. The pipe itself may be fabricated from a another rigid material such as aluminum or stainless steel, as long as the inner surfaces are coated or otherwise treated to be highly reflective. Preferably, the optical mixer 20 has a rectangular cross-section (as taken orthogonal to the longitudinal axis A—A of the mixer 20 and the collimator 22), although other cross-sectional shapes, such as other polygonal shapes or circular or elliptical shapes, may be employed in alternative embodiments. The inner walls of the optical mixer 20 are substantially parallel to the longitudinal axis A—A of the mixer 20 and the collimator 22. The highly reflective and substantially parallel inner walls of the mixer 20 maximize the number of times the infrared energy E will be reflected between the walls of the mixer 20, thoroughly mixing the infrared energy E as it propagates through the mixer 20. In a presently preferred embodiment, the mixer 20 is about 1.2 inches to 2.4 inches in length and its cross-section is a rectangle of about 0.4 inches by about 0.6 inches. Of course, other dimensions may be employed in constructing the mixer 20. In particular it is be advantageous to miniaturize the mixer or otherwise make it as small as possible Still referring to FIG. 1, the collimator 22 comprises a tube with an inner surface coating which is highly reflective and minimally absorptive in infrared wavelengths, preferably a polished gold coating. The tube itself may be fabricated from a another rigid material such as aluminum, nickel or stainless steel, as long as the inner surfaces are coated or otherwise treated to be highly reflective. Preferably, the collimator 22 has a rectangular cross-section, although other cross-sectional shapes, such as other polygonal shapes or circular, parabolic or elliptical shapes, may be employed in alternative embodiments. The inner walls of the collimator 22 diverge as they extend away from the mixer 20. Preferably, the inner walls of the collimator 22 are substantially straight and form an angle of about 7 degrees with respect to the longitudinal axis A—A. The collimator 22 aligns the infrared energy E to propagate in a direction that is generally parallel to the longitudinal axis A—A of the mixer 20 and the collimator 22, so that the infrared energy E will strike the surface of the filters 24 at an angle as close to 90 degrees as possible.

In a presently preferred embodiment, the collimator is about 7.5 inches in length. At its narrow end 22a, the cross-section of the collimator 22 is a rectangle of about 0.4 inches by 0.6 inches. At its wide end 22b, the collimator 22 has a rectangular cross-section of about 1.8 inches by 2.6 inches. Preferably, the collimator 22 aligns the infrared energy E to an angle of incidence (with respect to the longitudinal axis A—A) of about 0–15 degrees before the energy E impinges upon the filters 24. Of course, other dimensions or incidence angles may be employed in constructing and operating the collimator 22.

With further reference to FIGS. 1 and 6A, each concentrator 26 comprises a tapered surface oriented such that its wide end 26a is adapted to receive the infrared energy exiting the corresponding filter 24, and such that its narrow end 26b is adjacent to the corresponding detector 28. The inward-facing surfaces of the concentrators 26 have an inner surface coating which is highly reflective and minimally absorptive in infrared wavelengths, preferably a polished gold coating. The concentrators 26 themselves may be fabricated from a another rigid material such as aluminum, nickel or stainless steel, so long as their inner surfaces are coated or otherwise treated to be highly reflective.

Preferably, the concentrators 26 have a rectangular cross-section (as taken orthogonal to the longitudinal axis A—A), although other cross-sectional shapes, such as other polygonal shapes or circular, parabolic or elliptical shapes, may be employed in alternative embodiments. The inner walls of the concentrators converge as they extend toward the narrow end 26b. Preferably, the inner walls of the collimators 26 are substantially straight and form an angle of about 8 degrees with respect to the longitudinal axis A—A. Such a configuration is adapted to concentrate infrared energy as it passes through the concentrators 26 from the wide end 26a to the narrow end 26b, before reaching the detectors 28.

In a presently preferred embodiment, each concentrator 26 is about 1.5 inches in length. At the wide end 26a, the cross-section of each concentrator 26 is a rectangle of about 0.6 inches by 0.57 inches. At the narrow end 26b, each concentrator 26 has a rectangular cross-section of about 0.177 inches by 0.177 inches. Of course, other dimensions or incidence angles may be employed in constructing the concentrators 26.

e. Filters

The filters 24 preferably comprise standard interference-type infrared filters, widely available from manufacturers such as Optical Coating Laboratory, Inc. ("OCLI") of Santa Rosa, Calif. In the embodiment illustrated in FIG. 1, a 3×4 array of filters 24 is positioned above a 3×4 array of detectors 28 and concentrators 26. As employed in this embodiment, the filters 24 are arranged in four groups of three filters having the same wavelength sensitivity. These four groups have bandpass center wavelengths of 7.15 $\mu$m±0.03 $\mu$m, 8.40 $\mu$m±0.03 $\mu$m, 9.48 $\mu$m±0.04 $\mu$m, and 11.10 $\mu$m±0.04 $\mu$m, respectively, which correspond to wavelengths around which water and glucose absorb electromagnetic radiation. Typical bandwidths for these filters range from 0.20 $\mu$m to 0.50 $\mu$m.

In an alternative embodiment, the array of wavelength-specific filters 24 may be replaced with a single Fabry-Perot interferometer, which can provide wavelength sensitivity which varies as a sample of infrared energy is taken from the material sample S. Thus, this embodiment permits the use of only one detector 28, the output signal of which varies in wavelength specificity over time. The output signal can be de-multiplexed based on the wavelength sensitivities induced by the Fabry-Perot interferometer, to provide a multiple-wavelength profile of the infrared energy emitted by the material sample S. In this embodiment, the optical mixer 20 may be omitted, as only one detector 28 need be employed.

In still other embodiments, the array of filters 24 may comprise a filter wheel that rotates different filters with varying wavelength sensitivities over a single detector 24. Alternatively, an electronically tunable infrared filter may be employed in a manner similar to the Fabry-Perot interferometer discussed above, to provide wavelength sensitivity which varies during the detection process. In either of these embodiments, the optical mixer 20 may be omitted, as only one detector 28 need be employed.

f. Detectors

The detectors 28 may comprise any detector type suitable for sensing infrared energy, preferably in the mid-infrared wavelengths. For example, the detectors 28 may comprise mercury-cadmium-telluride (MCT) detectors. A detector such as a Fermionics (Simi Valley, Calif.) model PV-9.1 with a PVA481-1 pre-amplifier is acceptable. Similar units from other manufacturers such as Graseby (Tampa, Fla.) can be substituted. Other suitable components for use as the detectors 28 include pyroelectric detectors, thermopiles, bolometers, silicon microbolometers and lead-salt focal plane arrays.

g. Control System

Figure 7:
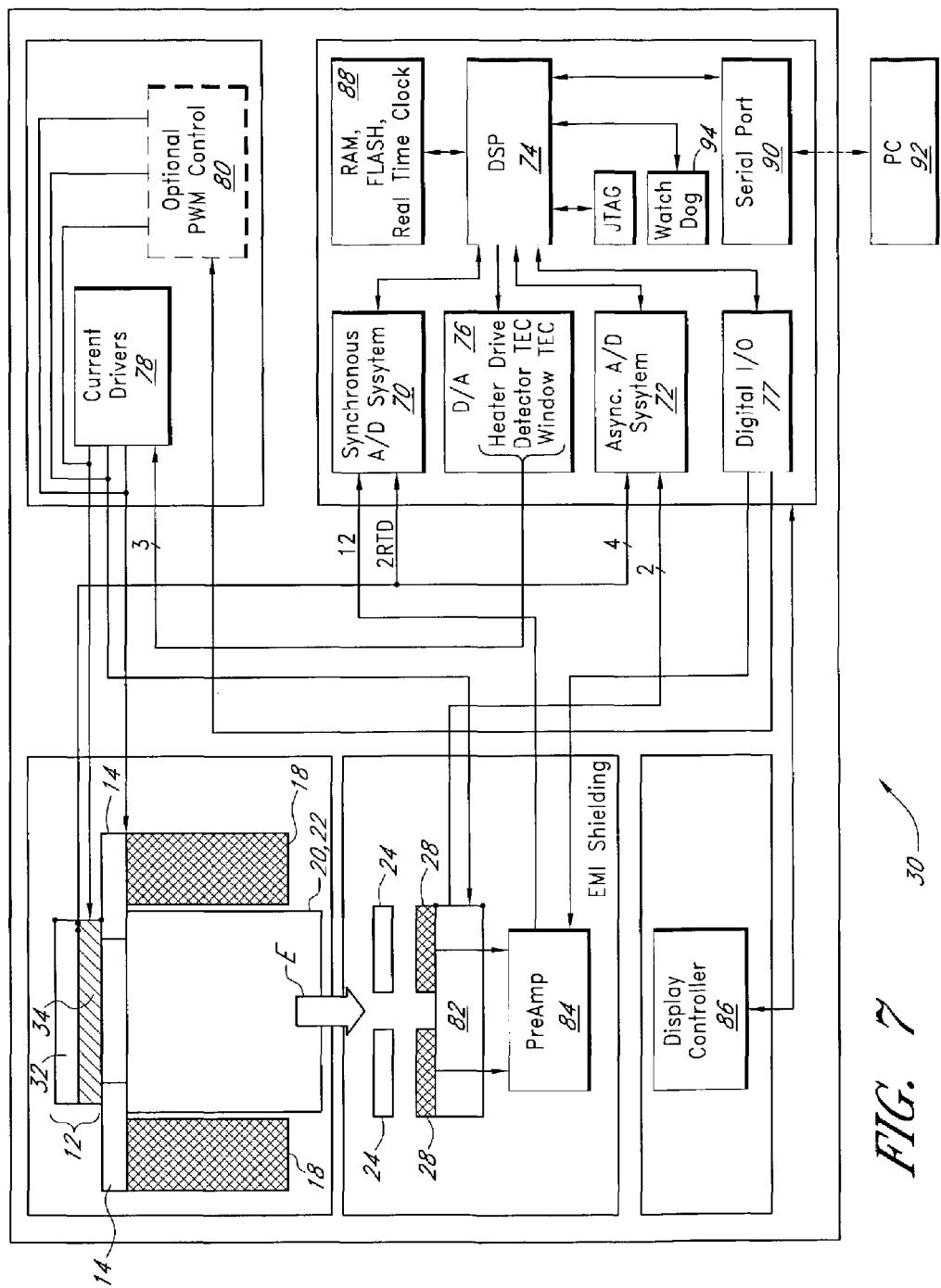
FIG. 7 is a schematic view of a control system for use with the noninvasive optical detection system.

FIG. 7 depicts the control system 30 in greater detail, as well as the interconnections between the control system and other relevant portions of the noninvasive system. The control system includes a temperature control subsystem and a data acquisition subsystem.

In the temperature control subsystem, temperature sensors (such as RTDs and/or thermistors) located in the window assembly 12 provide a window temperature signal to a synchronous analog-to-digital conversion system 70 and an asynchronous analog-to-digital conversion system 72. The A/D systems 70, 72 in turn provide a digital window temperature signal to a digital signal processor (DSP) 74. The processor 74 executes a window temperature control algorithm and determines appropriate control inputs for the heater layer 34 of the window assembly 12 and/or for the cooling system 14, based on the information contained in the window temperature signal. The processor 74 outputs one or more digital control signals to a digital-to-analog conversion system 76 which in turn provides one or more analog control signals to current drivers 78. In response to the control signal(s), the current drivers 78 regulate the power supplied to the heater layer 34 and/or to the cooling system 14. In one embodiment, the processor 74 provides a control signal through a digital I/O device 77 to a pulse-width modulator (PWM) control 80, which provides a signal that controls the operation of the current drivers 78. Alternatively, a low-pass filter (not shown) at the output of the PWM provides for continuous operation of the current drivers 78.

In another embodiment, temperature sensors may be located at the cooling system 14 and appropriately connected to the A/D system(s) and processor to provide closed-loop control of the cooling system as well.

In yet another embodiment, a detector cooling system 82 is located in thermally conductive relation to one or more of the detectors 28. The detector cooling system 82 may comprise any of the devices disclosed above as comprising the cooling system 14, and preferably comprises a Peltier-type thermoelectric device. The temperature control subsystem may also include temperature sensors, such as RTDs and/or thermistors, located in or adjacent to the detector cooling system 82, and electrical connections between these sensors and the asynchronous A/D system 72. The temperature sensors of the detector cooling system 82 provide detector temperature signals to the processor 74. In one embodiment, the detector cooling system 82 operates independently of the window temperature control system, and the detector cooling system temperature signals are sampled using the asynchronous A/D system 72. In accordance with the temperature control algorithm, the processor 74 determines appropriate control inputs for the detector cooling system 82, based on the information contained in the detector temperature signal. The processor 74 outputs digital control signals to the D/A system 76 which in turn provides analog control signals to the current drivers 78. In response to the control signals, the current drivers 78 regulate the power supplied to the detector cooling system 14. In one embodiment, the processor 74 also provides a control signal through the digital I/O device 77 and the PWM control 80, to control the operation of the detector cooling system 82 by the current drivers 78. Alternatively, a low-pass filter (not shown) at the output of the PWM provides for continuous operation of the current drivers 78.

In the data acquisition subsystem, the detectors 28 respond to the infrared energy E incident thereon by passing one or more analog detector signals to a preamp 84. The preamp 84 amplifies the detector signals and passes them to the synchronous A/D system 70, which converts the detector signals to digital form and passes them to the processor 74. The processor 74 determines the concentrations of the analyte(s) of interest, based on the detector signals and a concentration-analysis algorithm and/or phase/concentration regression model stored in a memory module 88. The concentration-analysis algorithm and/or phase/concentration regression model may be developed according to any of the analysis methodologies discussed herein. The processor may communicate the concentration results and/or other information to a display controller 86, which operates a display (not shown), such as an LCD display, to present the information to the user.

A watchdog timer 94 may be employed to ensure that the processor 74 is operating correctly. If the watchdog timer 94 does not receive a signal from the processor 74 within a specified time, the watchdog timer 94 resets the processor 74. The control system may also include a JTAG interface 96 to enable testing of the noninvasive system 10.

In one embodiment, the synchronous A/D system 70 comprises a 20-bit, 14 channel system, and the asynchronous A/D system 72 comprises a 16-bit, 16 channel system. The preamp may comprise a 12-channel preamp corresponding to an array of 12 detectors 28.

The control system may also include a serial port 90 or other conventional data port to permit connection to a personal computer 92. The personal computer can be employed to update the algorithm(s) and/or phase/concentration regression model(s) stored in the memory module 88, or to download a compilation of analyte-concentration data from the noninvasive system. A real-time clock or other timing device may be accessible by the processor 74 to make any time-dependent calculations which may be desirable to a user.

2. Analysis Methodology

The detector(s) 28 of the noninvasive system 10 are used to detect the infrared energy emitted by the material sample S in various desired wavelengths. At each measured wavelength, the material sample S emits infrared energy at an intensity which varies over time. The time-varying intensities arise largely in response to the use of the window assembly 12 (including its heater layer 34) and the cooling system 14 to induce a thermal gradient in the material sample S. As used herein, "thermal gradient" is a broad term and is used in its ordinary sense and refers, without limitation, to a difference in temperature and/or thermal energy between different locations, such as different depths, of a material sample, which can be induced by any suitable method of increasing or decreasing the temperature and/or thermal energy in one or more locations of the sample. As will be discussed in detail below, the concentration of an analyte of interest (such as glucose) in the material sample S can be determined with a device such as the noninvasive system 10, by comparing the time-varying intensity profiles of the various measured wavelengths.

Analysis methodologies are discussed herein within the context of detecting the concentration of glucose within a material sample, such as a tissue sample, which includes a large proportion of water. However, it will evident that these methodologies are not limited to this context and may be applied to the detection of a wide variety of analytes within a wide variety of sample types. It should also be understood that other suitable analysis methodologies and suitable variations of the disclosed methodologies may be employed in operating an analyte detection system, such as the non-invasive system 10.

Figure 8:
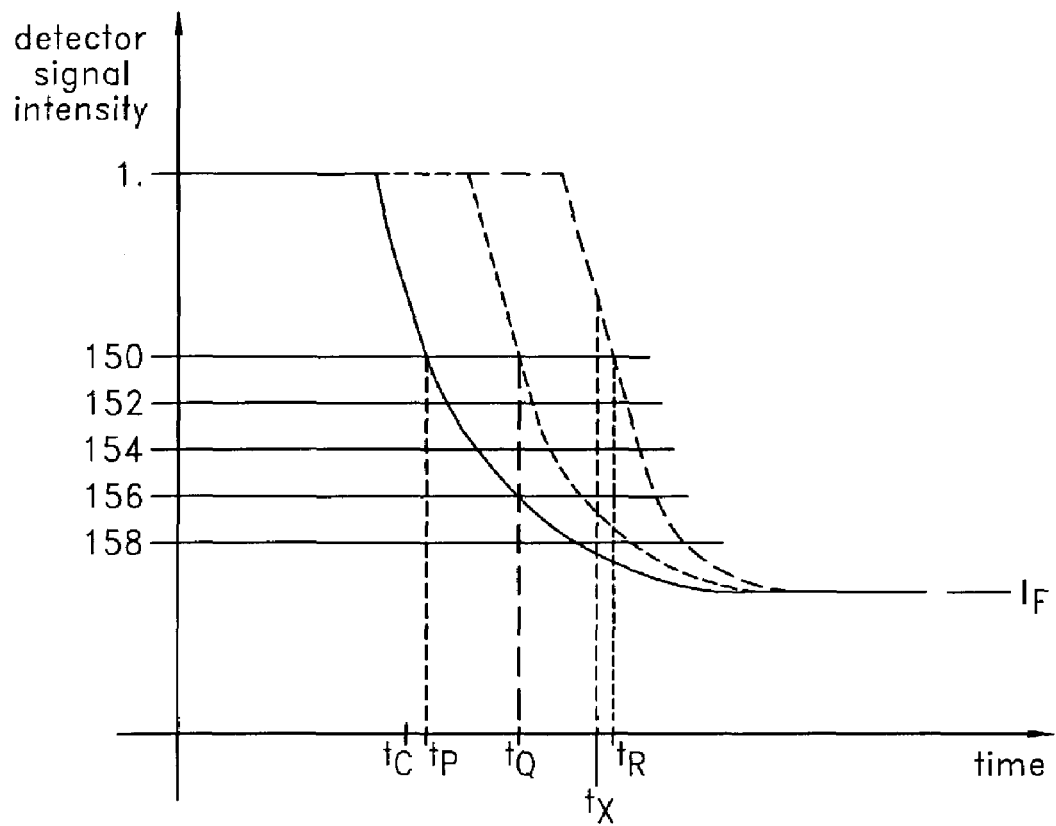
FIG. 8 depicts a first methodology for determining the concentration of an analyte of interest.

As shown in FIG. 8, a first reference signal P may be measured at a first reference wavelength. The first reference signal P is measured at a wavelength where water strongly absorbs (e.g., 2.9 µm or 6.1 µm). Because water strongly absorbs radiation at these wavelengths, the detector signal intensity is reduced at those wavelengths. Moreover, at these wavelengths water absorbs the photon emissions emanating from deep inside the sample. The net effect is that a signal emitted at these wavelengths from deep inside the sample is not easily detected. The first reference signal P is thus a good indicator of thermal-gradient effects near the sample surface and may be known as a surface reference signal. This signal may be calibrated and normalized, in the absence of heating or cooling applied to the sample, to a baseline value of 1. For greater accuracy, more than one first reference wavelength may be measured. For example, both 2.9 µm and 6.1 µm may be chosen as first reference wavelengths.

As further shown in FIG. 8, a second reference signal R may also be measured. The second signal R may be measured at a wavelength where water has very low absorbance (e.g., 3.6 µm or 4.2 µm). This second reference signal R thus provides the analyst with information concerning the deeper regions of the sample, whereas the first signal P provides information concerning the sample surface. This signal may also be calibrated and normalized, in the absence of heating or cooling applied to the sample, to a baseline value of 1. As with the first (surface) reference signal P, greater accuracy may be obtained by using more than one second (deep) reference signal R.

In order to determine analyte concentration, a third (analytical) signal Q is also measured. This signal is measured at an IR absorbance peak of the selected analyte. The IR absorbance peaks for glucose are in the range of about 6.5 µm to 11.0 µm. This detector signal may also be calibrated and normalized, in the absence of heating or cooling applied to the material sample S, to a baseline value of 1. As with the reference signals P, R, the analytical signal Q may be measured at more than one absorbance peak.

Optionally, or additionally, reference signals may be measured at wavelengths that bracket the analyte absorbance peak. These signals may be advantageously monitored at reference wavelengths which do not overlap the analyte absorbance peaks. Further, it is advantageous to measure reference wavelengths at absorbance peaks which do not overlap the absorbance peaks of other possible constituents contained in the sample.

a. Basic Thermal Gradient

As further shown in FIG. 8, the signal intensities P, Q, R are shown initially at the normalized baseline signal intensity of 1. This of course reflects the baseline radiative behavior of a test sample in the absence of applied heating or cooling. At a time $t_C$, the surface of the sample is subjected to a temperature event which induces a thermal gradient in the sample. The gradient can be induced by heating or cooling the sample surface. The example shown in FIG. 8 uses cooling, for example, using a 10° C. cooling event. In response to the cooling event, the intensities of the detector signals P, Q, R decrease over time.

Since the cooling of the sample is neither uniform nor instantaneous, the surface cools before the deeper regions of the sample cool. As each of the signals P, Q, R drop in intensity, a pattern emerges. Signal intensity declines as expected, but as the signals P, Q, R reach a given amplitude value (or series of amplitude values: 150, 152, 154, 156, 158), certain temporal effects are noted. After the cooling event is induced at $t_C$, the first (surface) reference signal P declines in amplitude most rapidly, reaching a checkpoint 150 first, at time $t_P$. This is due to the fact that the first reference signal P mirrors the sample's radiative characteristics near the surface of the sample. Since the sample surface cools before the underlying regions, the surface (first) reference signal P drops in intensity first.

Simultaneously, the second reference signal R is monitored. Since the second reference signal R corresponds to the radiation characteristics of deeper regions of the sample, which do not cool as rapidly as the surface (due to the time needed for the surface cooling to propagate into the deeper regions of the sample), the intensity of signal R does not decline until slightly later. Consequently, the signal R does not reach the magnitude 150 until some later time $t_R$. In other words, there exists a time delay between the time $t_P$ at which the amplitude of the first reference signal P reaches the checkpoint 150 and the time $t_R$ at which the second reference signal R reaches the same checkpoint 150. This time delay can be expressed as a phase difference $\Phi(\lambda)$. Additionally, a phase difference may be measured between the analytical signal Q and either or both reference signals P, R.

As the concentration of analyte increases, the amount of absorbance at the analytical wavelength increases. This reduces the intensity of the analytical signal Q in a concentration-dependent way. Consequently, the analytical signal Q reaches intensity 150 at some intermediate time $t_Q$. The higher the concentration of analyte, the more the analytical signal Q shifts to the left in FIG. 8. As a result, with increasing analyte concentration, the phase difference $\Phi(\lambda)$ decreases relative to the first (surface) reference signal P and increases relative to the second (deep tissue) reference signal R. The phase difference(s) $\Phi(\lambda)$ are directly related to analyte concentration and can be used to make accurate determinations of analyte concentration.

The phase difference $\Phi(\lambda)$ between the first (surface) reference signal P and the analytical signal Q is represented by the equation:

$$\Phi(\lambda)=|t_P-t_Q|$$

The magnitude of this phase difference decreases with increasing analyte concentration.

The phase difference $\Phi(\lambda)$ between the second (deep tissue) reference signal R and the analytical signal Q signal is represented by the equation:

$$\Phi(\lambda)=|t_Q-t_R|$$

The magnitude of this phase difference increases with increasing analyte concentration.

Accuracy may be enhanced by choosing several checkpoints, for example, 150, 152, 154, 156, and 158 and averaging the phase differences observed at each checkpoint. The accuracy of this method may be further enhanced by integrating the phase difference(s) continuously over the entire test period. Because in this example only a single temperature event (here, a cooling event) has been induced, the sample reaches a new lower equilibrium temperature and the signals stabilize at a new constant level $I_F$. Of course, the method works equally well with thermal gradients induced by heating or by the application or introduction of other forms of energy, such as but not limited to, light, radiation, chemically induced heat, friction and vibration.

This methodology is not limited to the determination of phase difference. At any given time (for example, at a time $t_X$) the amplitude of the analytical signal Q may be compared to the amplitude of either or both of the reference signals P, R. The difference in amplitude may be observed and processed to determine analyte concentration.

This method, the variants disclosed herein, and the apparatus disclosed as suitable for application of the method(s), are not limited to the detection of in-vivo glucose concentration. The method and disclosed variants and apparatus may be used on human, animal, or even plant subjects, or on organic or inorganic compositions in a non-medical setting. The method may be used to take measurements of in-vivo or in-vitro samples of virtually any kind. The method is useful for measuring the concentration of a wide range of additional chemical analytes, including but not limited to, glucose, ethanol, insulin, water, carbon dioxide, blood oxygen, cholesterol, bilirubin, ketones, fatty acids, lipoproteins, albumin, urea, creatinine, white blood cells, red blood cells, hemoglobin, oxygenated hemoglobin, carboxyhemoglobin, organic molecules, inorganic molecules, pharmaceuticals, cytochrome, various proteins and chromophores, microcalcifications, hormones, as well as other chemical compounds. To detect a given analyte, one needs only to select appropriate analytical and reference wavelengths.

The method is adaptable and may be used to determine chemical concentrations in samples of body fluids (e.g., blood, urine or saliva) once they have been extracted from a patient. In fact, the method may be used for the measurement of in-vitro samples of virtually any kind.

b. Modulated Thermal Gradient

In some embodiments of the methodology described above, a periodically modulated thermal gradient can be employed to make accurate determinations of analyte concentration.

As previously shown in FIG. 8, once a thermal gradient is induced in the sample, the reference and analytical signals P, Q, R fall out of phase with respect to each other. This phase difference $\Phi(\lambda)$ is present whether the thermal gradient is induced through heating or cooling. By alternatively subjecting the test sample to cyclic pattern of heating, cooling, or alternately heating and cooling, an oscillating thermal gradient may be induced in a sample for an extended period of time.

Figure 9:
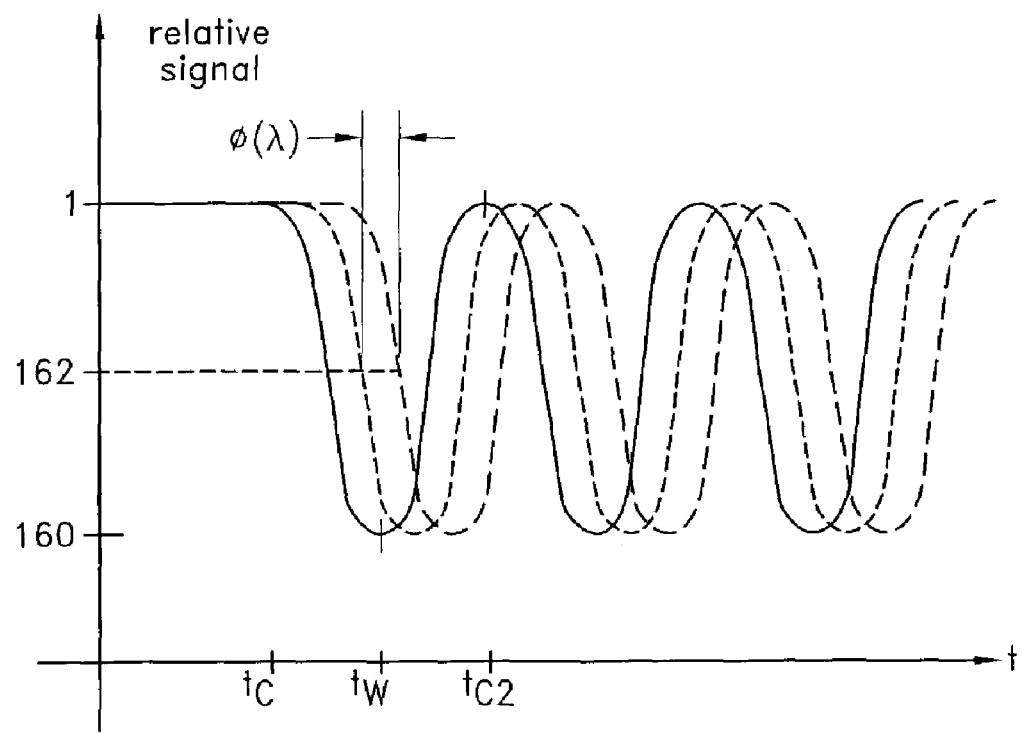
FIG. 9 depicts a second methodology for determining the concentration of an analyte of interest.

An oscillating thermal gradient is illustrated using a sinusoidally modulated gradient. FIG. 9 depicts detector signals emanating from a test sample. As with the methodology shown in FIG. 8, one or more reference signals J, L are measured. One or more analytical signals K are also monitored. These signals may be calibrated and normalized, in the absence of heating or cooling applied to the sample, to a baseline value of 1. FIG. 9 shows the signals after normalization. At some time $t_C$, a temperature event (e.g., cooling) is induced at the sample surface. This causes a decline in the detector signal. As shown in FIG. 8, the signals (P, Q, R) decline until the thermal gradient disappears and a new equilibrium detector signal $I_F$ is reached. In the method shown in FIG. 9, as the gradient begins to disappear at a signal intensity 160, a heating event, at a time $t_W$, is induced in the sample surface. As a result the detector output signals J, K, L will rise as the sample temperature rises. At some later time $t_{C2}$, another cooling event is induced, causing the temperature and detector signals to decline. This cycle of cooling and heating may be repeated over a time interval of arbitrary length. Moreover, if the cooling and heating events are timed properly, a periodically modulated thermal gradient may be induced in the test sample.

As previously explained in the discussions relating to FIG. 8, the phase difference $\Phi(\lambda)$ may be measured and used to determine analyte concentration. FIG. 9 shows that the first (surface) reference signal J declines and rises in intensity first. The second (deep tissue) reference signal L declines and rises in a time-delayed manner relative to the first reference signal J. The analytical signal K exhibits a time/phase delay dependent on the analyte concentration. With increasing concentration, the analytical signal K shifts to the left in FIG. 9. As with FIG. 8, the phase difference $\Phi(\lambda)$ may be measured. For example, a phase difference $\Phi(\lambda)$ between the second reference signal L and the analytical signal K, may be measured at a set amplitude 162 as shown in FIG. 9. Again, the magnitude of the phase signal reflects the analyte concentration of the sample.

The phase-difference information compiled by any of the methodologies disclosed herein can be correlated by the control system 30 (see FIG. 1) with previously determined phase-difference information to determine the analyte concentration in the sample. This correlation could involve comparison of the phase-difference information received from analysis of the sample, with a data set containing the phase-difference profiles observed from analysis of wide variety of standards of known analyte concentration. In one embodiment, a phase/concentration curve or regression model is established by applying regression techniques to a set of phase-difference data observed in standards of known analyte concentration. This curve is used to estimate the analyte concentration in a sample based on the phase-difference information received from the sample.

Advantageously, the phase difference $\Phi(\lambda)$ may be measured continuously throughout the test period. The phase-difference measurements may be integrated over the entire test period for an extremely accurate measure of phase difference $\Phi(\lambda)$. Accuracy may also be improved by using more than one reference signal and/or more than one analytical signal.

As an alternative or as a supplement to measuring phase difference(s), differences in amplitude between the analytical and reference signal(s) may be measured and employed to determine analyte concentration. Additional details relating to this technique and not necessary to repeat here may be found in the Assignee's U.S. patent application Ser. No. 09/538,164, incorporated by reference below.

Additionally, these methods may be advantageously employed to simultaneously measure the concentration of one or more analytes. By choosing reference and analyte wavelengths that do not overlap, phase differences can be simultaneously measured and processed to determine analyte concentrations. Although FIG. 9 illustrates the method used in conjunction with a sinusoidally modulated thermal gradient, the principle applies to thermal gradients conforming to any periodic function. In more complex cases, analysis using signal processing with Fourier transforms or other techniques allows accurate determinations of phase difference $\Phi(\lambda)$ and analyte concentration.

Figure 10:
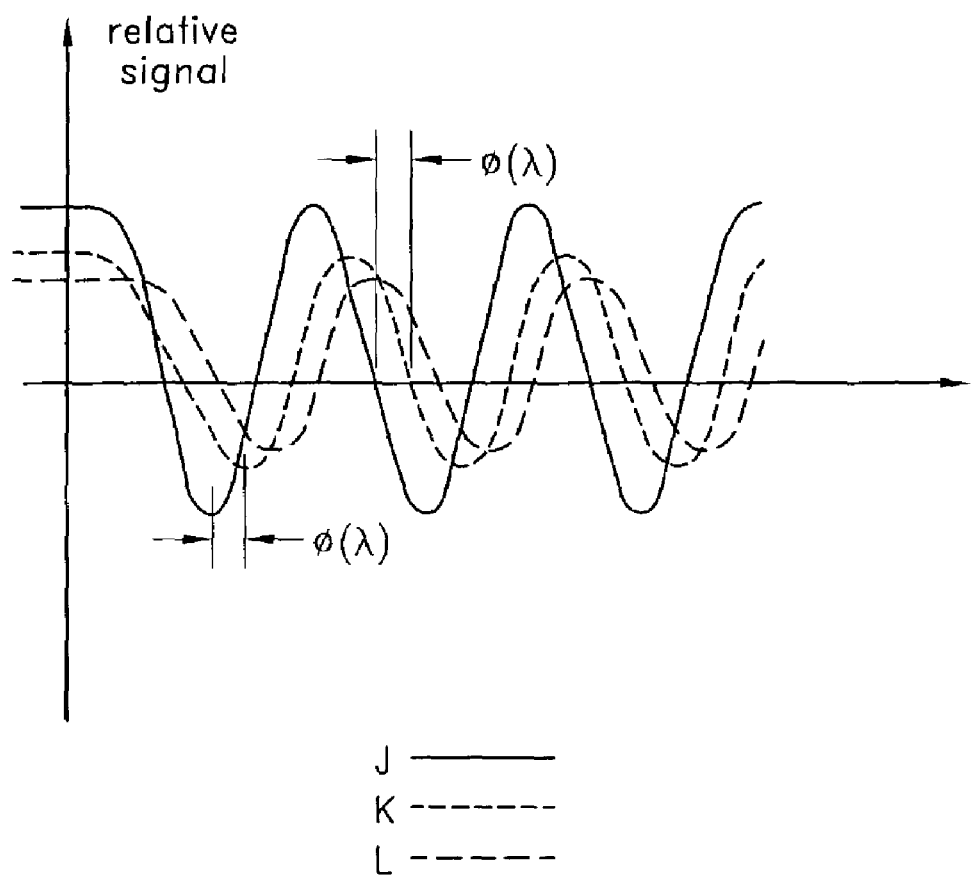
FIG. 10 depicts a third methodology for determining the concentration of an analyte of interest.

As shown in FIG. 10, the magnitude of the phase differences may be determined by measuring the time intervals between the amplitude peaks (or troughs) of the reference signals J, L and the analytical signal K. Alternatively, the time intervals between the "zero crossings" (the point at which the signal amplitude changes from positive to negative, or negative to positive) may be used to determine the phase difference between the analytical signal K and the reference signals J, L. This information is subsequently processed and a determination of analyte concentration may then be made. This particular method has the advantage of not requiring normalized signals.

As a further alternative, two or more driving frequencies may be employed to determine analyte concentrations at selected depths within the sample. A slow (e.g., 1 Hz) driving frequency creates a thermal gradient which penetrates deeper into the sample than the gradient created by a fast (e.g., 3 Hz) driving frequency. This is because the individual heating and/or cooling events are longer in duration where the driving frequency is lower. Thus, the use of a slow driving frequency provides analyte-concentration information from a deeper "slice" of the sample than does the use of a fast driving frequency.

It has been found that when analyzing a sample of human skin, a temperature event of 10° C. creates a thermal gradient which penetrates to a depth of about 150 $\mu$m, after about 500 ms of exposure. Consequently, a cooling/heating cycle or driving frequency of 1 Hz provides information to a depth of about 150 $\mu$m. It has also been determined that exposure to a temperature event of 10° C. for about 167 ms creates a thermal gradient that penetrates to a depth of about 50 $\mu$m. Therefore, a cooling/heating cycle of 3 Hz provides information to a depth of about 50 $\mu$m. By subtracting the detector signal information measured at a 3 Hz driving frequency from the detector signal information measured at a 1 Hz driving frequency, one can determine the analyte concentration(s) in the region of skin between 50 and 150 $\mu$m. Of course, a similar approach can be used to determine analyte concentrations at any desired depth range within any suitable type of sample.

Figure 11:
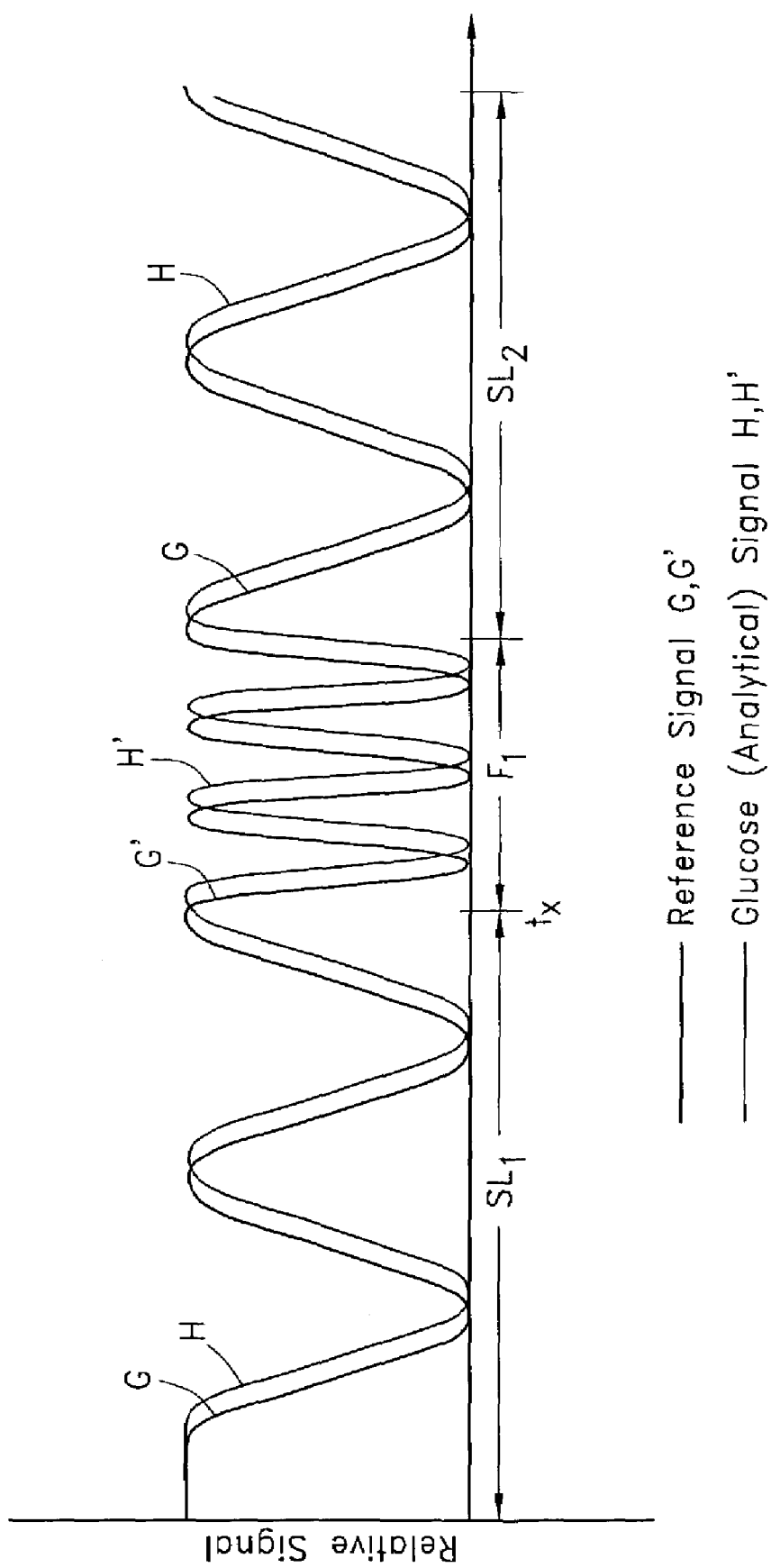
FIG. 11 depicts a fourth methodology for determining the concentration of an analyte of interest.

As shown in FIG. 11, alternating deep and shallow thermal gradients may be induced by alternating slow and fast driving frequencies. As with the methods described above, this variation also involves the detection and measurement of phase differences $\Phi(\lambda)$ between reference signals G, G' and analytical signals H, H'. Phase differences are measured at both fast (e.g., 3 Hz) and slow (e.g., 1 Hz) driving frequencies. The slow driving frequency may continue for an arbitrarily chosen number of cycles (in region $SL_1$), for example, two full cycles. Then the fast driving frequency is employed for a selected duration, in region $F_1$. The phase difference data is compiled in the same manner as disclosed above. In addition, the fast frequency (shallow sample) phase difference data may be subtracted from the slow frequency (deep sample) data to provide an accurate determination of analyte concentration in the region of the sample between the gradient penetration depth associated with the fast driving frequency and that associated with the slow driving frequency.

Figure 12:
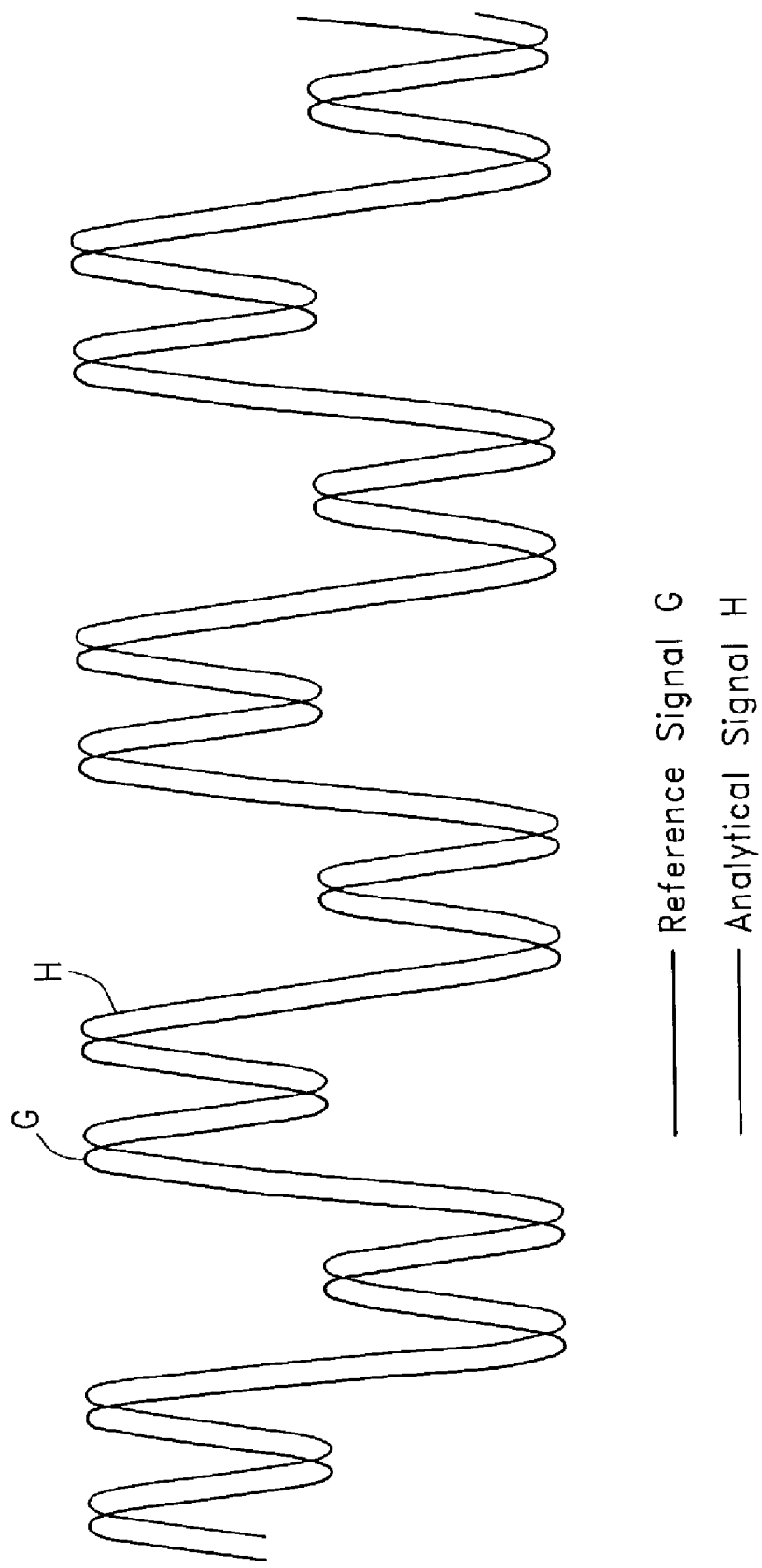
FIG. 12 depicts a fifth methodology for determining the concentration of an analyte of interest.

The driving frequencies (e.g., 1 Hz and 3 Hz) can be multiplexed as shown in FIG. 12. The fast (3 Hz) and slow (1 Hz) driving frequencies can be superimposed rather than sequentially implemented. During analysis, the data can be separated by frequency (using Fourier transform or other techniques) and independent measurements of phase delay at each of the driving frequencies may be calculated. Once resolved, the two sets of phase delay data are processed to determine absorbance and analyte concentration.

Additional details not necessary to repeat here may be found in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. Pat. No. 5,877,500, titled MULTICHANNEL INFRARED DETECTOR WITH OPTICAL CONCENTRATORS FOR EACH CHANNEL, issued on Mar. 2, 1999; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; U.S. Provisional Patent Application No. 60/336,404, filed Oct. 29, 2001, titled WINDOW ASSEMBLY; U.S. Provisional Patent Application No. 60/340,435, filed Dec. 12, 2001, titled CONTROL SYSTEM FOR BLOOD CONSTITUENT MONITOR; U.S. Provisional Patent Application No. 60/340,654, filed Dec. 12, 2001, titled SYSTEM AND METHOD FOR CONDUCTING AND DETECTING INFRARED RADIATION; U.S. Provisional Patent Application No. 60/336,294, filed Oct. 29, 2001, titled METHOD AND DEVICE FOR INCREASING ACCURACY OF BLOOD CONSTITUENT MEASUREMENT; and U.S. Provisional Patent Application No. 60/339,116, filed Nov. 7, 2001, titled METHOD AND APPARATUS FOR IMPROVING CLINICALLY SIGNIFICANT ACCURACY OF ANALYTE MEASUREMENTS. The entire disclosure of all of the above-mentioned patents, patent applications and publications is hereby incorporated by reference herein and made a part of this specification.

B. Whole-Blood Detection System

FIG. 13 is a schematic view of a reagentless whole-blood analyte detection system 200 (hereinafter "whole-blood system") in a preferred configuration. The whole-blood system 200 may comprise a radiation source 220, a filter 230, a cuvette 240 that includes a sample cell 242, and a radiation detector 250. The whole-blood system 200 preferably also comprises a signal processor 260 and a display 270. Although a cuvette 240 is shown here, other sample elements, as described below, could also be used in the system 200. The whole-blood system 200 can also comprise a sample extractor 280, which can be used to access bodily fluid from an appendage, such as the finger 290, forearm, or any other suitable location.

As used herein, the terms "whole-blood analyte detection system" and "whole-blood system" are broad, synonymous terms and are used in their ordinary sense and refer, without limitation, to analyte detection devices which can determine the concentration of an analyte in a material sample by passing electromagnetic radiation into the sample and detecting the absorbance of the radiation by the sample. As used herein, the term "wholeblood" is a broad term and is used in its ordinary sense and refers, without limitation, to blood that has been withdrawn from a patient but that has not been otherwise processed, e.g., it has not been hemolysed, lyophilized, centrifuged, or separated in any other manner, after being removed from the patient. Whole-blood may contain amounts of other fluids, such as interstitial fluid or intracellular fluid, which may enter the sample during the withdrawal process or are naturally present in the blood. It should be understood, however, that the whole-blood system 200 disclosed herein is not limited to analysis of whole-blood, as the whole-blood system 10 may be employed to analyze other substances, such as saliva, urine, sweat, interstitial fluid, intracellular fluid, hemolysed, lyophilized, or centrifuged blood or any other organic or inorganic materials.

The whole-blood system 200 may comprise a near-patient testing system. As used herein, "near-patient testing system" is a broad term and is used in its ordinary sense, and includes, without limitation, test systems that are configured to be used where the patient is rather than exclusively in a laboratory, e.g., systems that can be used at a patient's home, in a clinic, in a hospital, or even in a mobile environment. Users of near-patient testing systems can include patients, family members of patients, clinicians, nurses, or doctors. A "near-patient testing system" could also include a "point-of-care" system.

The whole-blood system 200 may in one embodiment be configured to be operated easily by the patient or user. As such, the system 200 is preferably a portable device. As used herein, "portable" is a broad term and is used in its ordinary sense and means, without limitation, that the system 200 can be easily transported by the patient and used where convenient. For example, the system 200 is advantageously small. In one preferred embodiment, the system 200 is small enough to fit into a purse or backpack. In another embodiment, the system 200 is small enough to fit into a pants pocket. In still another embodiment, the system 200 is small enough to be held in the palm of a hand of the user.

Some of the embodiments described herein employ a sample element to hold a material sample, such as a sample of biological fluid. As used herein, "sample element" is a broad term and is used in its ordinary sense and includes, without limitation, structures that have a sample cell and at least one sample cell wall, but more generally includes any of a number of structures that can hold, support or contain a material sample and that allow electromagnetic radiation to pass through a sample held, supported or contained thereby; e.g., a cuvette, test strip, etc. As used herein, the term "disposable" when applied to a component, such as a sample element, is a broad term and is used in its ordinary sense and means, without limitation, that the component in question is used a finite number of times and then discarded. Some disposable components are used only once and then discarded. Other disposable components are used more than once and then discarded.

The radiation source 220 of the whole-blood system 200 emits electro-magnetic radiation in any of a number of spectral ranges, e.g., within infrared wavelengths; in the mid-infrared wavelengths; above about 0.8 $\mu$m; between about 5.0 $\mu$m and about 20.0 m; and/or between about 5.25 $\mu$m and about 12.0 $\mu$m. However, in other embodiments the whole-blood system 200 may employ a radiation source 220 which emits in wavelengths found anywhere from the visible spectrum through the microwave spectrum, for example anywhere from about 0.4 $\mu$m to greater than about 100 $\mu$m. In still further embodiments the radiation source emits electromagnetic radiation in wavelengths between about 3.5 $\mu$m and about 14 $\mu$m, or between about 0.8 $\mu$m and about 2.5 $\mu$m, or between about 2.5 $\mu$m and about 20 $\mu$m, or between about 20 $\mu$m and about 100 $\mu$m, or between about 6.85 $\mu$m and about 10.10 $\mu$m.

The radiation emitted from the source 220 is in one embodiment modulated at a frequency between about one-half hertz and about one hundred hertz, in another embodiment between about 2.5 hertz and about 7.5 hertz, in still another embodiment at about 50 hertz, and in yet another embodiment at about 5 hertz. With a modulated radiation source, ambient light sources, such as a flickering fluorescent lamp, can be more easily identified and rejected when analyzing the radiation incident on the detector 250. One source that is suitable for this application is produced by ION OPTICS, INC. and sold under the part number NL5LNC.

The filter 230 permits electromagnetic radiation of selected wavelengths to pass through and impinge upon the cuvette/sample element 240. Preferably, the filter 230 permits radiation at least at about the following wavelengths to pass through to the cuvette/sample element: 3.9, 4.0 $\mu$m, 4.05 $\mu$m, 4.2 $\mu$m, 4.75, 4.95 $\mu$m, 5.25 $\mu$m, 6.12 $\mu$m, 7.4 $\mu$m, 8.0 $\mu$m, 8.45 $\mu$m, 9.25 $\mu$m, 9.5 $\mu$m, 9.65 $\mu$m, 10.4 $\mu$m, 12.2 $\mu$m. In another embodiment, the filter 230 permits radiation at least at about the following wavelengths to pass through to the cuvette/sample element: 5.25 $\mu$m, 6.12 $\mu$m, 6.8 $\mu$m, 8.03 $\mu$m, 8.45 $\mu$m, 9.25 $\mu$m, 9.65 $\mu$m, 10.4 $\mu$m, 12 $\mu$m. In still another embodiment, the filter 230 permits radiation at least at about the following wavelengths to pass through to the cuvette/sample element: 6.85 $\mu$m, 6.97 $\mu$m, 7.39 $\mu$m, 8.23 $\mu$m, 8.62 $\mu$m, 9.02 $\mu$m, 9.22 $\mu$m, 9.43 $\mu$m, 9.62 $\mu$m, and 10.10 $\mu$m. The sets of wavelengths recited above correspond to specific embodiments within the scope of this disclosure. Furthermore, other subsets of the foregoing sets or other combinations of wavelengths can be selected. Finally, other sets of wavelengths can be selected within the scope of this disclosure based on cost of production, development time, availability, and other factors relating to cost, manufacturability, and time to market of the filters used to generate the selected wavelengths, and/or to reduce the total number of filters needed.

In one embodiment, the filter 230 is capable of cycling its passband among a variety of narrow spectral bands or a variety of selected wavelengths. The filter 230 may thus comprise a solid-state tunable infrared filter, such as that available from ION OPTICS INC. The filter 230 could also be implemented as a filter wheel with a plurality of fixed-passband filters mounted on the wheel, generally perpendicular to the direction of the radiation emitted by the source 220. Rotation of the filter wheel alternately presents filters that pass radiation at wavelengths that vary in accordance with the filters as they pass through the field of view of the detector 250.

The detector 250 preferably comprises a 3 mm long by 3 mm wide pyroelectric detector. Suitable examples are produced by DIAS Angewandte Sensorik GmbH of Dresden, Germany, or by BAE Systems (such as its TGS model detector). The detector 250 could alternatively comprise a thermopile, a bolometer, a silicon microbolometer, a lead-salt focal plane array, or a mercury-cadmium-telluride (MCT) detector. Whichever structure is used as the detector 250, it is desirably configured to respond to the radiation incident upon its active surface 254 to produce electrical signals that correspond to the incident radiation.

In one embodiment, the sample element comprises a cuvette 240 which in turn comprises a sample cell 242 configured to hold a sample of tissue and/or fluid (such as whole-blood, blood components, interstitial fluid, intercellular fluid, saliva, urine, sweat and/or other organic or inorganic materials) from a patient within its sample cell. The cuvette 240 is installed in the whole-blood system 200 with the sample cell 242 located at least partially in the optical path 243 between the radiation source 220 and the detector 250. Thus, when radiation is emitted from the source 220 through the filter 230 and the sample cell 242 of the cuvette 240, the detector 250 detects the radiation signal strength at the wavelength(s) of interest. Based on this signal strength, the signal processor 260 determines the degree to which the sample in the cell 242 absorbs radiation at the detected wavelength(s). The concentration of the analyte of interest is then determined from the absorption data via any suitable spectroscopic technique.

As shown in FIG. 13, the whole-blood system 200 can also comprise a sample extractor 280. As used herein, the term "sample extractor" is a broad term and is used in its ordinary sense and refers, without limitation, to any device which is suitable for drawing a sample material, such as whole-blood, other bodily fluids, or any other sample material, through the skin of a patient. In various embodiments, the sample extractor may comprise a lance, laser lance, iontophoretic sampler, gas-jet, fluid-jet or particle-jet perforator, ultrasonic enhancer (used with or without a chemical enhancer), or any other suitable device.

As shown in FIG. 13, the sample extractor 280 could form an opening in an appendage, such as the finger 290, to make whole-blood available to the cuvette 240. It should be understood that other appendages could be used to draw the sample, including but not limited to the forearm. With some embodiments of the sample extractor 280, the user forms a tiny hole or slice through the skin, through which flows a sample of bodily fluid such as whole-blood. Where the sample extractor 280 comprises a lance (see FIG. 14), the sample extractor 280 may comprise a sharp cutting implement made of metal or other rigid materials. One suitable laser lance is the Lasette Plus® produced by Cell Robotics International, Inc. of Albuquerque, N. Mex. If a laser lance, iontophoretic sampler, gas-jet or fluid-jet perforator is used as the sample extractor 280, it could be incorporated into the whole-blood system 200 (see FIG. 13), or it could be a separate device.

Additional information on laser lances can be found in U.S. Pat. No. 5,908,416, issued Jun. 1, 1999, titled LASER DERMAL PERFORATOR; the entirety of this patent is hereby incorporated by reference herein and made a part of this specification. One suitable gas-jet, fluid-jet or particle-jet perforator is disclosed in U.S. Pat. No. 6,207,400, issued Mar. 27, 2001, titled NON- OR MINIMALLY INVASIVE MONITORING METHODS USING PARTICLE DELIVERY METHODS; the entirety of this patent is hereby incorporated by reference herein and made a part of this specification. One suitable iontophoretic sampler is disclosed in U.S. Pat. No. 6,298,254, issued Oct. 2, 2001, titled DEVICE FOR SAMPLING SUBSTANCES USING ALTERNATING POLARITY OF IONTOPHORETIC CURRENT; the entirety of this patent is hereby incorporated by reference herein and made a part of this specification. One suitable ultrasonic enhancer, and chemical enhancers suitable for use therewith, are disclosed in U.S. Pat. No. 5,458,140, titled ENHANCEMENT OF TRANSDERMAL MONITORING APPLICATIONS WITH ULTRASOUND AND CHEMICAL ENHANCERS, issued Oct. 17, 1995, the entire disclosure of which is hereby incorporated by reference and made a part of this specification.

FIG. 14 shows one embodiment of a sample element, in the form of a cuvette 240, in greater detail. The cuvette 240 further comprises a sample supply passage 248, a pierceable portion 249, a first window 244, and a second window 246, with the sample cell 242 extending between the windows 244, 246. In one embodiment, the cuvette 240 does not have a second window 246. The first window 244 (or second window 246) is one form of a sample cell wall; in other embodiments of the sample elements and cuvettes disclosed herein, any sample cell wall may be used that at least partially contains, holds or supports a material sample, such as a biological fluid sample, and which is transmissive of at least some bands of electromagnetic radiation, and which may but need not be transmissive of electromagnetic radiation in the visible range. The pierceable portion 249 is an area of the sample supply passage 248 that can be pierced by suitable embodiments of the sample extractor 280. Suitable embodiments of the sample extractor 280 can pierce the portion 249 and the appendage 290 to create a wound in the appendage 290 and to provide an inlet for the blood or other fluid from the wound to enter the cuvette 240. (The sample extractor 280 is shown on the opposite side of the sample element in FIG. 14, as compared to FIG. 13, as it may pierce the portion 249 from either side.)

The windows 244, 246 are preferably optically transmissive in the range of electromagnetic radiation that is emitted by the source 220, or that is permitted to pass through the filter 230. In one embodiment, the material that makes up the windows 244, 246 is completely transmissive, i.e., it does not absorb any of the electromagnetic radiation from the source 220 and filter 230 that is incident upon it. In another embodiment, the material of the windows 244, 246 has some absorption in the electromagnetic range of interest, but its absorption is negligible. In yet another embodiment, the absorption of the material of the windows 244, 246 is not negligible, but it is known and stable for a relatively long period of time. In another embodiment, the absorption of the windows 244, 246 is stable for only a relatively short period of time, but the whole-blood system 200 is configured to observe the absorption of the material and eliminate it from the analyte measurement before the material properties can change measurably.

The windows 244, 246 are made of polypropylene in one embodiment. In another embodiment, the windows 244, 246 are made of polyethylene. Polyethylene and polypropylene are materials having particularly advantageous properties for handling and manufacturing, as is known in the art. Also, polypropylene can be arranged in a number of structures, e.g., isotactic, atactic and syndiotactic, which may enhance the flow characteristics of the sample in the sample element. Preferably the windows 244, 246 are made of durable and easily manufactureable materials, such as the above-mentioned polypropylene or polyethylene, or silicon or any other suitable material. The windows 244, 246 can be made of any suitable polymer, which can be isotactic, atactic or syndiotactic in structure.

The distance between the windows 244, 246 comprises an optical pathlength and can be between about 1 $\mu$m and about 100 $\mu$m. In one embodiment, the optical pathlength is between about 10 $\mu$m and about 40 $\mu$m, or between about 25 $\mu$m and about 60 $\mu$m, or between about 30 $\mu$m and about 50 $\mu$m. In still another embodiment, the optical pathlength is about 25 $\mu$m. The transverse size of each of the windows 244, 246 is preferably about equal to the size of the detector 250. In one embodiment, the windows are round with a diameter of about 3 mm. In this embodiment, where the optical pathlength is about 25 $\mu$m the volume of the sample cell 242 is about 0.177 $\mu$L. In one embodiment, the length of the sample supply passage 248 is about 6 mm, the height of the sample supply passage 248 is about 1 mm, and the thickness of the sample supply passage 248 is about equal to the thickness of the sample cell, e.g., 25 $\mu$m. The volume of the sample supply passage is about 0.150 $\mu$L. Thus, the total volume of the cuvette 240 in one embodiment is about 0.327 $\mu$L. Of course, the volume of the cuvette 240/sample cell 242/etc. can vary, depending on many variables, such as the size and sensitivity of the detectors 250, the intensity of the radiation emitted by the source 220, the expected flow properties of the sample, and whether flow enhancers (discussed below) are incorporated into the cuvette 240. The transport of fluid to the sample cell 242 is achieved preferably through capillary action, but may also be achieved through wicking, or a combination of wicking and capillary action.

Figure 16A:
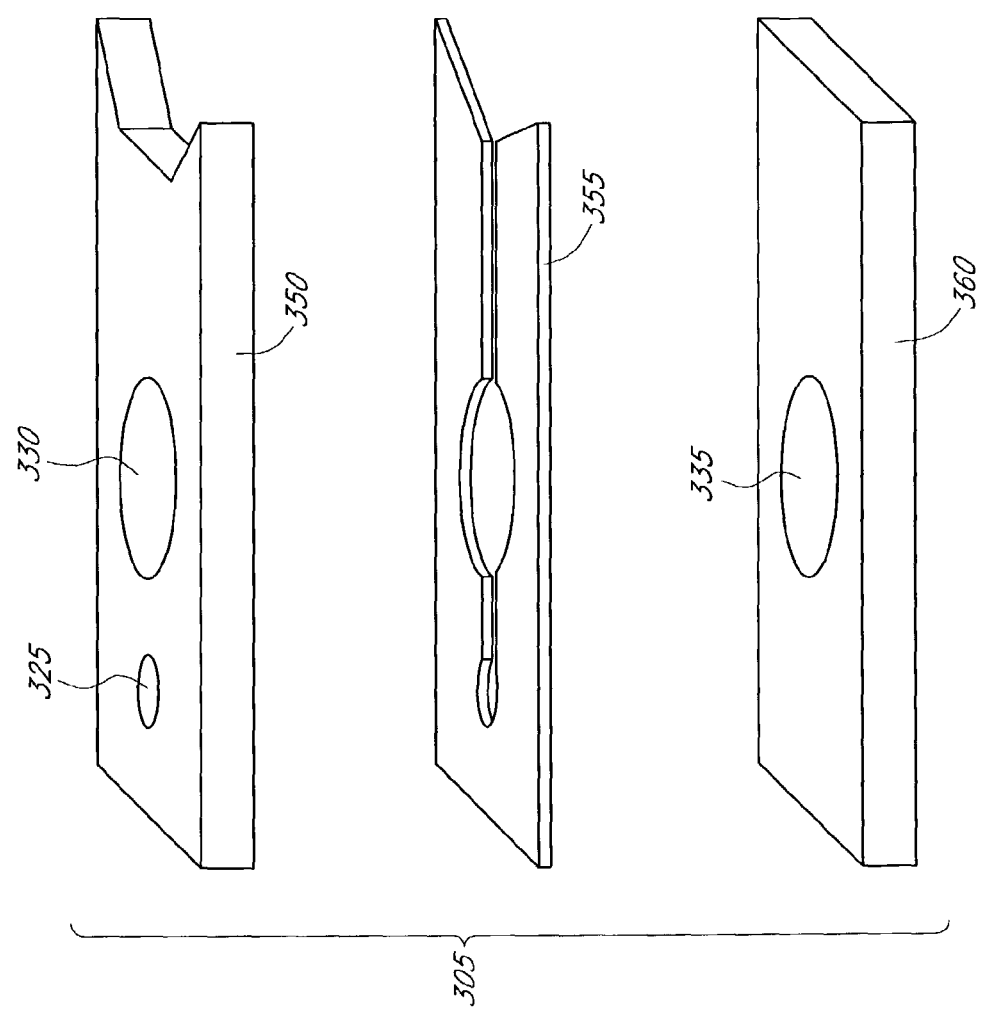
FIG. 16A is an exploded perspective view of the cuvette of FIG. 15.

FIGS. 15–17 depict another embodiment of a cuvette 305 that could be used in connection with the whole-blood system 200. The cuvette 305 comprises a sample cell 310, a sample supply passage 315, an air vent passage 320, and a vent 325. As best seen in FIGS. 16, 16A and 17, the cuvette also comprises a first sample cell window 330 having an inner side 332, and a second sample cell window 335 having an inner side 337. As discussed above, the window(s) 330/335 in some embodiments also comprise sample cell wall(s). The cuvette 305 also comprises an opening 317 at the end of the sample supply passage 315 opposite the sample cell 310. The cuvette 305 is preferably about ¼-⅛ inch wide and about ¾ inch long; however, other dimensions are possible while still achieving the advantages of the cuvette 305.

The sample cell 310 is defined between the inner side 332 of the first sample cell window 330 and the inner side 337 of the second sample cell window 335. The perpendicular distance T between the two inner sides 332, 337 comprises an optical pathlength that can be between about 1 $\mu$m and about 1.22 mm. The optical pathlength can alternatively be between about 1 $\mu$m and about 100 $\mu$m. The optical pathlength could still alternatively be about 80 $\mu$m, but is preferably between about 10 $\mu$m and about 50 $\mu$m. In another embodiment, the optical pathlength is about 25 $\mu$m. The windows 330, 335 are preferably formed from any of the materials discussed above as possessing sufficient radiation transmissivity. The thickness of each window is preferably as small as possible without overly weakening the sample cell 310 or cuvette 305.

Once a wound is made in the appendage 290, the opening 317 of the sample supply passage 315 of the cuvette 305 is placed in contact with the fluid that flows from the wound. In another embodiment, the sample is obtained without creating a wound, e.g. as is done with a saliva sample. In that case, the opening 317 of the sample supply passage 315 of the cuvette 305 is placed in contact with the fluid obtained without creating a wound. The fluid is then transported through the sample supply passage 315 and into the sample cell 310 via capillary action. The air vent passage 320 improves the capillary action by preventing the buildup of air pressure within the cuvette and allowing the blood to displace the air as the blood flows therein.

Other mechanisms may be employed to transport the sample to the sample cell 310. For example, wicking could be used by providing a wicking material in at least a portion of the sample supply passage 315. In another variation, wicking and capillary action could be used together to transport the sample to the sample cell 310. Membranes could also be positioned within the sample supply passage 315 to move the blood while at the same time filtering out components that might complicate the optical measurement performed by the whole-blood system 200.

FIGS. 16 and 16A depict one approach to constructing the cuvette 305. In this approach, the cuvette 305 comprises a first layer 350, a second layer 355, and a third layer 360. The second layer 355 is positioned between the first layer 350 and the third layer 360. The first layer 350 forms the first sample cell window 330 and the vent 325. As mentioned above, the vent 325 provides an escape for the air that is in the sample cell 310. While the vent 325 is shown on the first layer 350, it could also be positioned on the third layer 360, or could be a cutout in the second layer, and would then be located between the first layer 360 and the third layer 360 The third layer 360 forms the second sample cell window 335.

The second layer 355 may be formed entirely of an adhesive that joins the first and third layers 350, 360. In other embodiments, the second layer may be formed from similar materials as the first and third layers, or any other suitable material. The second layer 355 may also be formed as a carrier with an adhesive deposited on both sides thereof. The second layer 355 forms the sample supply passage 315, the air vent passage 320, and the sample cell 310. The thickness of the second layer 355 can be between about 1 $\mu$m and about 1.22 mm. This thickness can alternatively be between about 1 $\mu$m and about 100 $\mu$m. This thickness could alternatively be about 80 $\mu$m, but is preferably between about 10 $\mu$m and about 50 $\mu$m. In another embodiment, the second layer thickness is about 25 $\mu$m.

In other embodiments, the second layer 355 can be constructed as an adhesive film having a cutout portion to define the passages 315, 320, or as a cutout surrounded by adhesive.

Further information can be found in U.S. patent application Ser. No. 10/055,875, filed Jan. 21, 2002, titled REAGENT-LESS WHOLE-BLOOD GLUCOSE METER. The entire contents of this patent application is incorporated by reference herein and made a part of this specification.

II. Pathlength Insensitive Measurements

A variable optical pathlength algorithm facilitates pathlength insensitive measurements of blood constituents. This is to say that if the measurements are taken at the surface of a sample or at a depth of 90% of the sample, inside a cuvette or in living tissue, the readings are identical based on a mathematical correction process that applies known factors to the data before it is analyzed and a reading is given for the analyte in question.

Disclosed is a method that in certain embodiments accomplishes and solves all of the variable factors associated with taking blood analyte measurements in a blood sample, at any depth or thickness of sample, and compensating for said variables.

Figure 18:
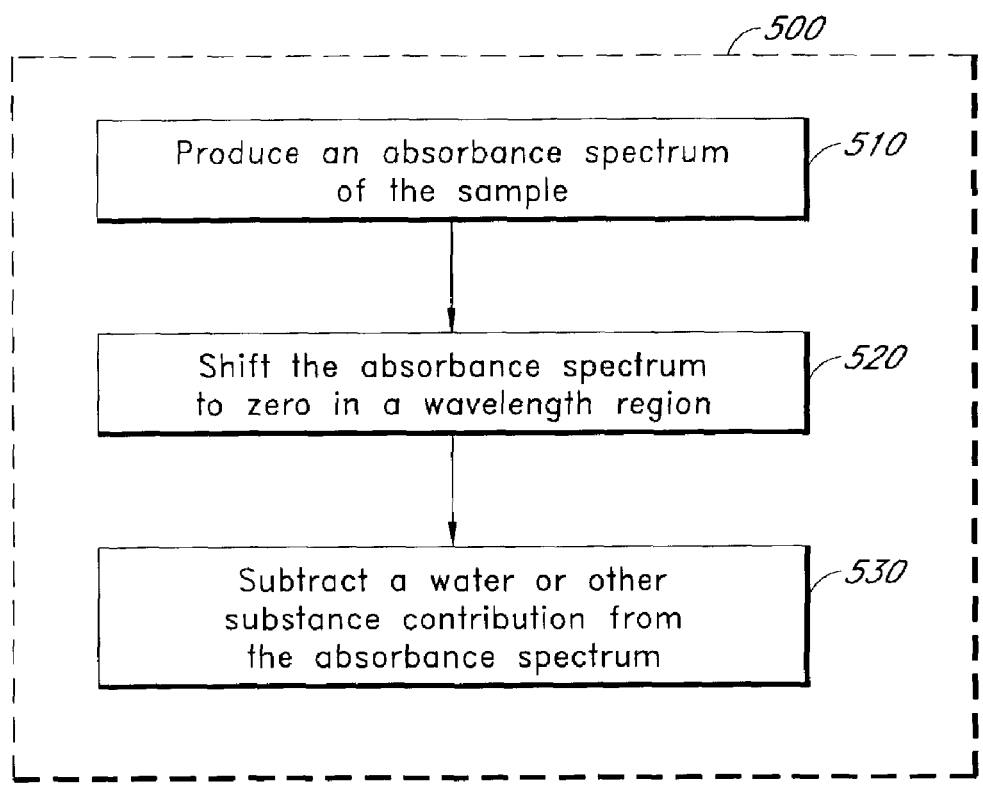
FIG. 18 is a flow diagram of one embodiment of a method for using spectroscopy to determine an analyte concentration in a sample.

FIG. 18 is a flow diagram of one embodiment of a method 500 for using spectroscopy to determine an analyte concentration in a sample. In an operational block 510, the method 500 comprises producing an absorbance spectrum of the sample. In an operational block 520, the method 500 further comprises shifting the absorbance spectrum to zero in a wavelength region. In an operational block 530, the method 500 further comprises subtracting a water or other substance contribution from the absorbance spectrum.

A. Experimental Set-Up

In an exemplary embodiment, the major components of blood were simulated using bovine serum albumin (BSA) for total blood protein and saline solution for serum. Infrared absorbance or optical density (OD) spectra of the samples were measured with a Fourier-Transform Infrared (FTIR) instrument from Perkin-Elmer, Inc. of Wellesley, Massachusetts. As used herein, the term "optical density" or "OD" is synonymous with the term "absorbance." Cuvette pathlength was set with different spacers between $BaF_2$ windows at 32 and 20 micrometers. The fringe pattern of the empty cuvette was used for calculation of the actual optical pathlength, which includes the pathlength traveled by the radiation inside the cuvette. Use of flexible tubing and the flow-through type of the cuvette allowed for repeated filling with different solutions without requiring changes to made to the experimental setup. Instrument drift (e.g., changes in optical pathlength) and baseline deviations were accounted for with saline reference measurements before and after sample measurements. A total of 100 scans were collected per sample over a period of about 5 minutes. Scanned data were stored in ASCII format and transferred to an electronic spreadsheet program (e.g., Lotus 1-2-3 from International Business Machines Corporation of Armonk, N.Y.) for processing and evaluation.

B. Results

Figure 19:
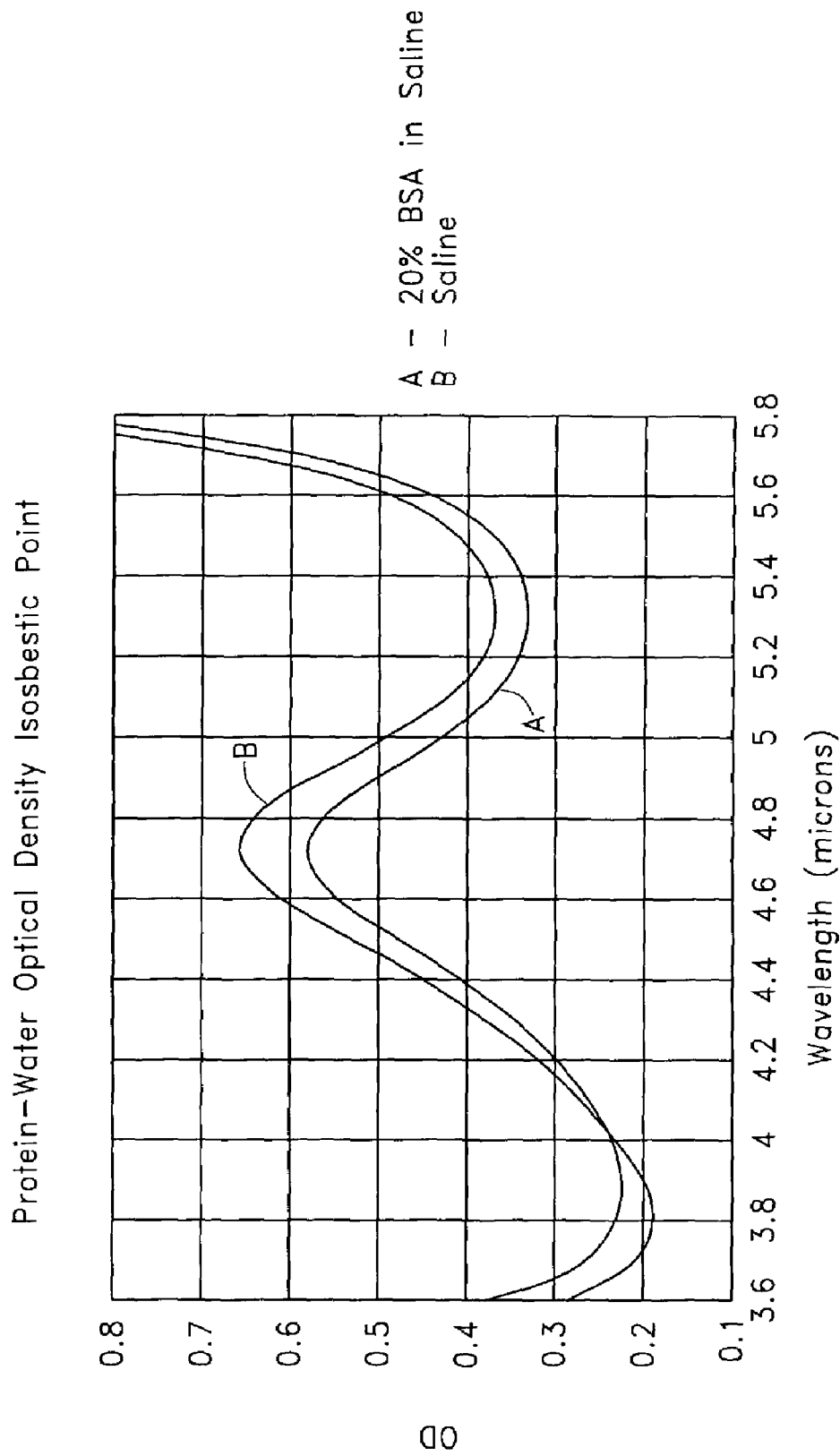
FIG. 19 is a graph illustrating one isosbestic point between approximately 4.0 and 4.2 $\mu$m in the absorbance spectra of water and whole blood protein.
Figure 20:
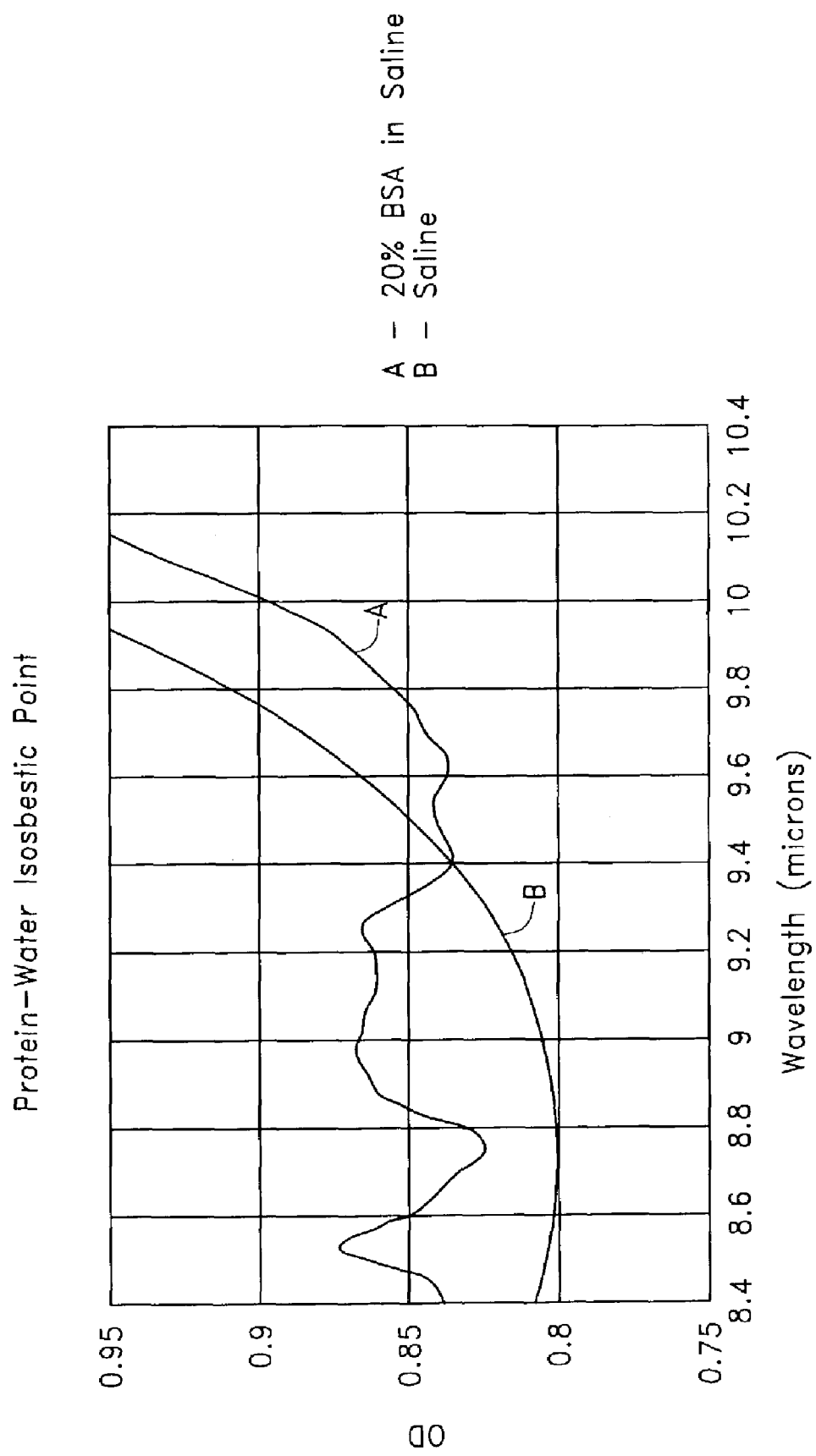
FIG. 20 is a graph illustrating another isosbestic point between approximately 9.2 $\mu$m and 9.6 $\mu$m in the absorbance spectra of water and whole blood protein.

It was discovered that changes of the protein to water ratio, equivalent to changes of hematocrit in blood, produce at least 2 isosbestic points on the wavelength scale, where the components protein and water exhibit identical IR absorbance, one of them at about 4 $\mu$m and the other at about 9.4 $\mu$m for BSA in water. As seen in FIG. 19 and FIG. 20, the effective isosbestic point can be expected to be somewhat different for different proteins in different solutions. The important and unexpected aspect of this observation is that these wavelength ranges can be used to obtain a current measure of effective optical pathlength in the filled cuvette, either before or during measurements at other wavelength ranges. Such information is very useful in subsequent calculations for compensation of instrument-related pathlength non-linearities.

Figure 21:
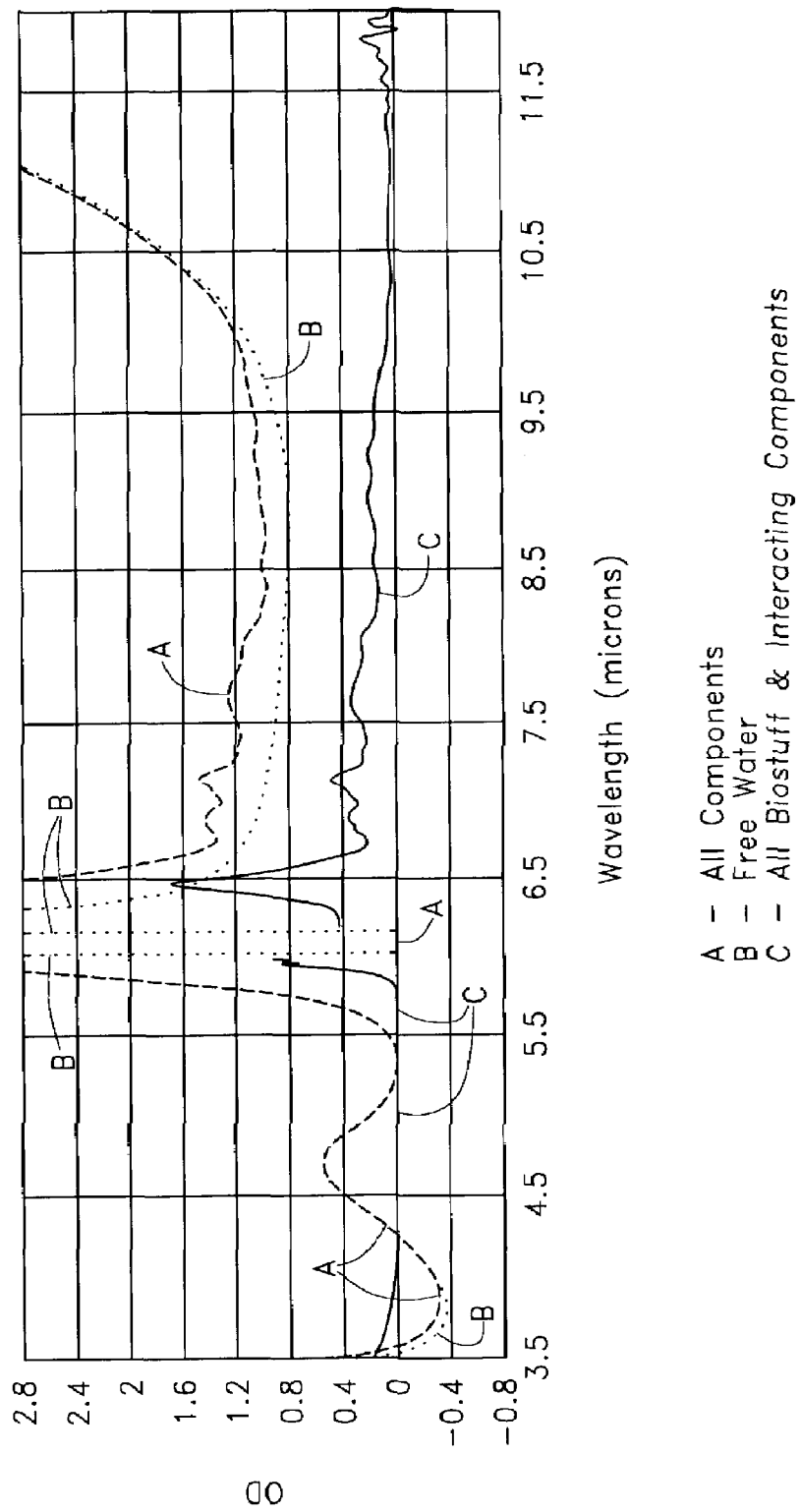
FIG. 21 is a graph illustrating progressive removal of free water contributions from an absorbance spectrum of a sample.

It was also discovered that after setting transmittance to zero at one or both wavelengths ranges of high water absorbance at 6.08 and/or 12.25 $\mu$m, thereby shifting absorbance to zero preferably at the lower isosbestic point, will result in spectral data at baseline. In FIG. 21, we can see the higher isosbestic point which may be used also but it is partially contaminated with absorbances of blood components that are present at low concentration levels.

It was also discovered that the absorbance peak centered around 4.7 $\mu$m, is almost entirely due to free water absorbance and can be advantageously used for determination of free water in the sample: the correct subtraction of absorbance of a stored reference water across the entire wavelength range is achieved when there is zero residual absorbance left between approximately 4.5 and 5 $\mu$m, shown in FIG. 21.

It was also discovered that prior knowledge of optical pathlength based on the total sample absorbance at the isosbestic point and/or based on water (e.g., saline) absorbance between approximately 4.5 and 5 $\mu$m, for example, allows for the use of the correct reference water spectrum that is compensated for nonlinearities at all wavelengths. Use of the correct reference spectrum is advantageous for distortion-free presentation of final results.

Figure 22:
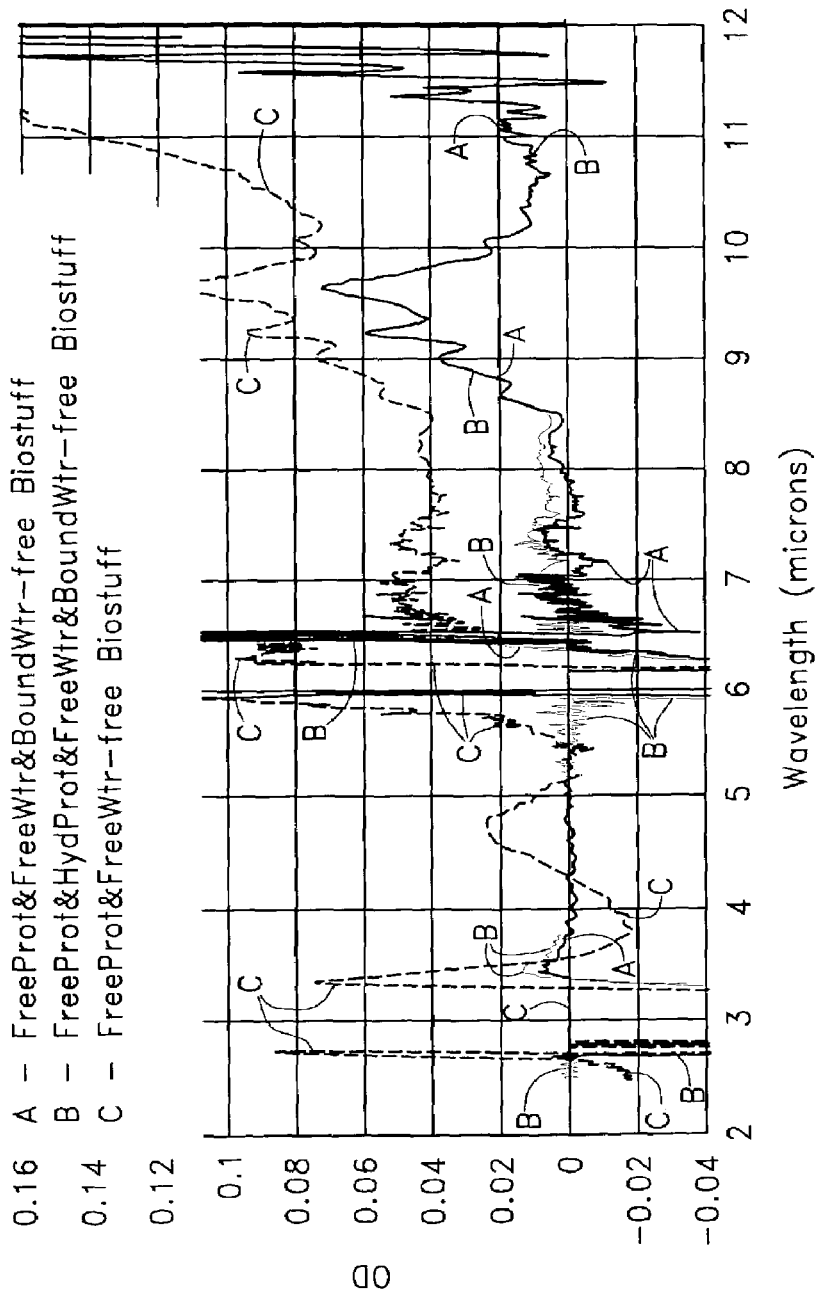
FIG. 22 is a graph illustrating determination of free protein from an absorbance spectrum of a sample.

It was also discovered that the absorbance peak centered around 7.1 $\mu$m, is almost entirely due to free protein absorbance and can be advantageously used for determination of free protein in the sample: the correct subtraction of absorbance of a stored reference hydrated protein across the entire wavelength range is achieved when there is zero residual absorbance left between approximately 7.0 and 7.2 $\mu$m or alternatively, at a different protein absorbance such as the range from approximately 7.9 to 8.1 $\mu$m or alternatively, a predefined residual at a combination of wavelength ranges, as shown in FIG. 22.

It was also discovered that prior knowledge of optical pathlength, based on the total sample absorbance at an isosbestic point and/or based on total protein absorbance between approximately 7.2 and 7.0 $\mu$m, or alternatively, on a different wavelength range of protein absorbance such as the range from approximately 7.9 to 8.1 $\mu$m, allows for the use of the correct reference protein spectrum that is compensated for nonlinearities at all wavelengths. Use of the correct reference spectrum is advantageous for distortion-free presentation of final results.

Figure 23:
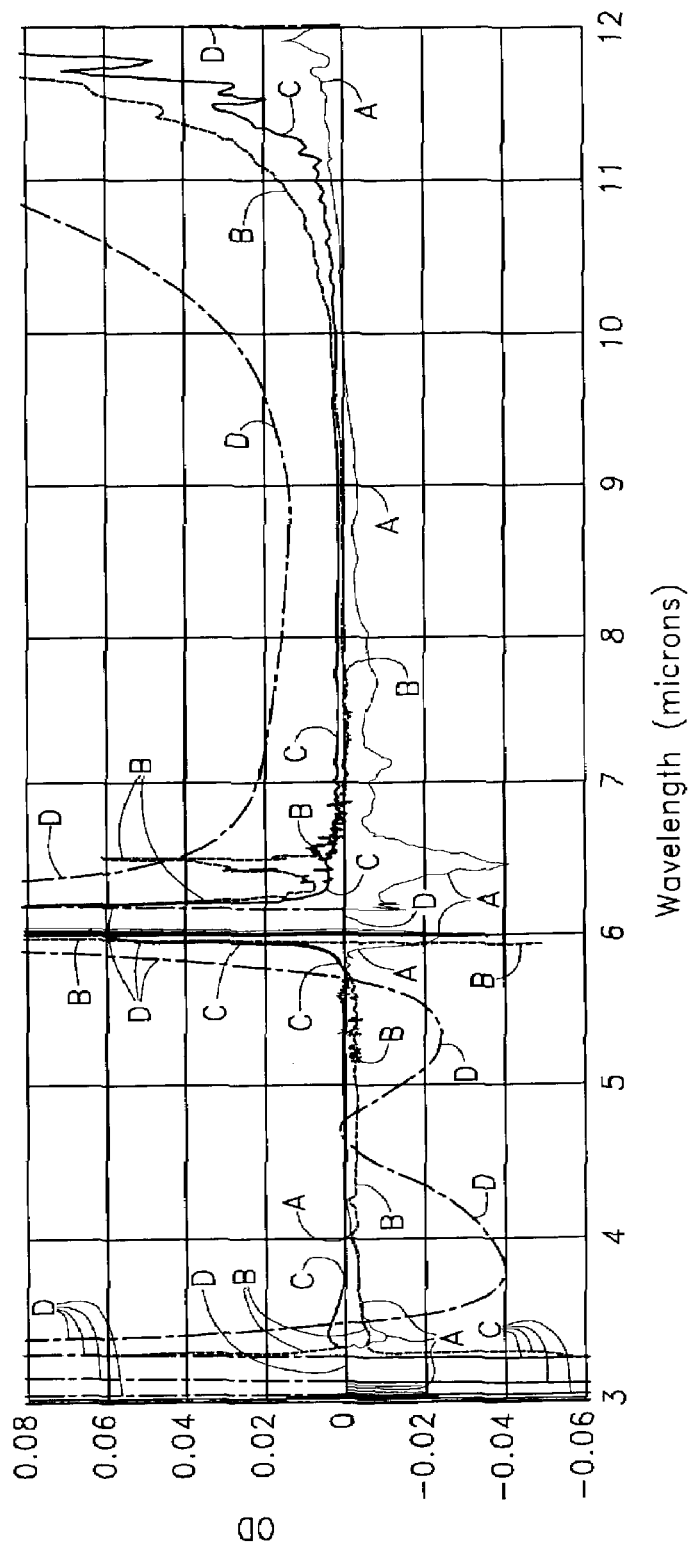
FIG. 23 is a graph illustrating progressive removal of residual interactive component contributions from an absorbance spectrum of a sample.

FIG. 23 shows that it was also discovered that repetition of the last two steps of water and protein removal from the complete sample, will result in further removal of smaller residual interactive components, most likely representing components of the boundary layer between water and protein.

Figure 24:
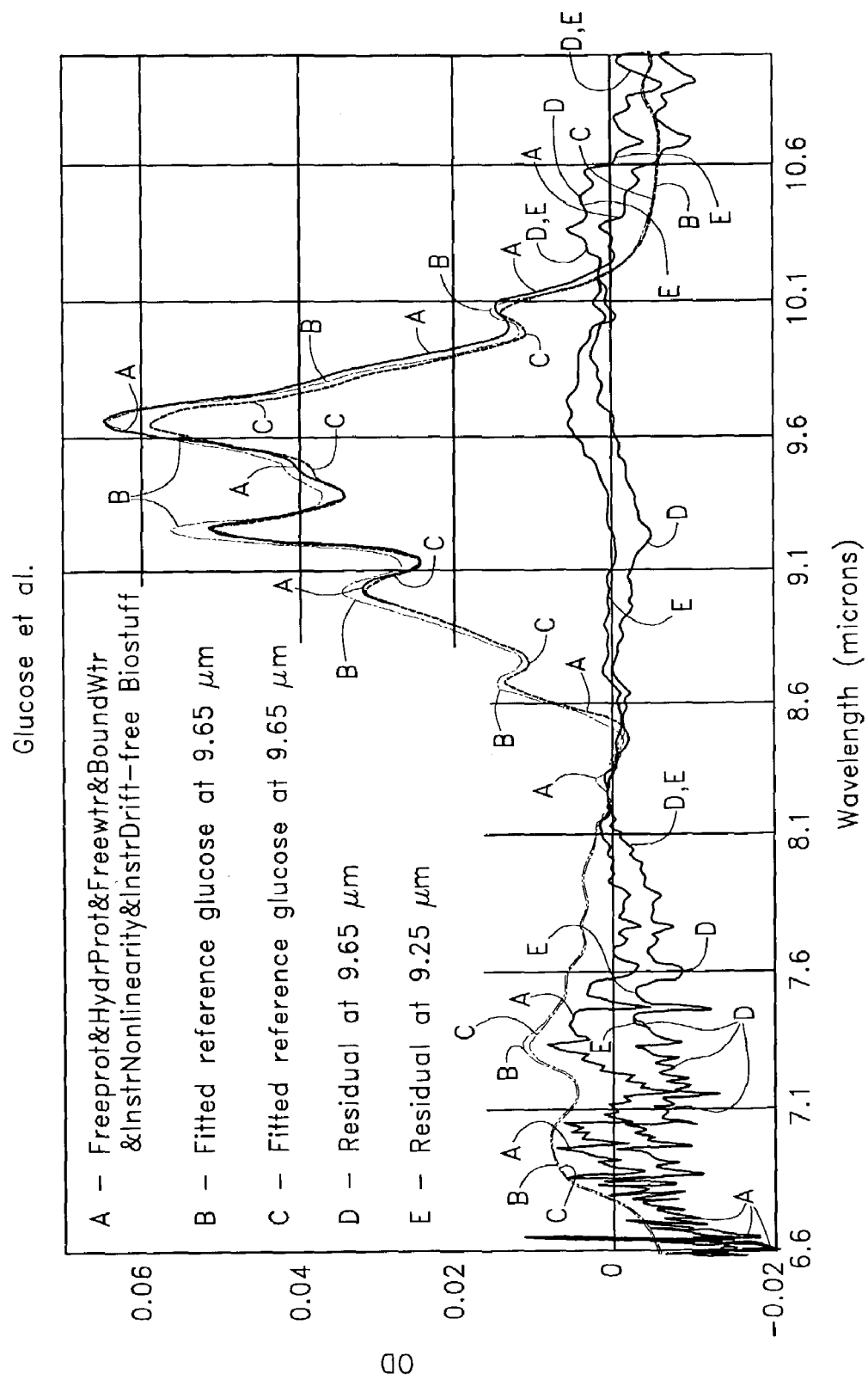
FIG. 24 is a graph illustrating an absorbance spectrum with residual absorbance after glucose spectral data removal used for individual determination of residual components.

It was also discovered that the resulting instrument drift corrected, water-, protein-, interactive components-removed, and optical pathlength and major component induced distortion-free spectral data can be fitted with reference glucose spectral data at one or more glucose absorbance maxima such as 9.25 and 9.65 $\mu$m to yield a measure for glucose in the original sample. The residual absorbance after glucose spectral data removal may be used further for individual determination of residual components. In certain embodiments, the residual components include high molecular weight substances, including but not limited to, other proteins, albumin, hemoglobin, fibrinogen, lipoproteins, and trasferrin. In certain other embodiments, the residual components include low molecular weight substances, including but not limited to, urea, lactate, and vitamin C. The final glucose measure may be corrected for the presence of such lower level potentially interfering substances by subtracting reference spectra of specific substances, such as urea, from the residual data, as shown in FIG. 24.

It was also discovered that by following the definition of glucose in blood, i.e. a measure of glucose per volume of sample, a useful measure for glucose concentration is obtained from algorithmically derived IR quantities as described above, by dividing the final glucose quantity by total water, total protein or alternatively a combination of both.

The methods disclosed herein may be used in connection with apparatus and or methods disclosed in U.S. Pat. No. 6,198,949, titled SOLID-STATE NON-INVASIVE INFRARED ABSORPTION SPECTROMETER FOR THE GENERATION AND CAPTURE OF THERMAL GRADIENT SPECTRA FROM LIVING TISSUE, issued Mar. 6, 2001; U.S. Pat. No. 6,161,028, titled METHOD FOR DETERMINING ANALYTE CONCENTRATION USING PERIODIC TEMPERATURE MODULATION AND PHASE DETECTION, issued Dec. 12, 2000; U.S. patent application Ser. No. 09/538,164, filed Mar. 30, 2000 and titled METHOD AND APPARATUS FOR DETERMINING ANALYTE CONCENTRATION USING PHASE AND MAGNITUDE DETECTION OF A RADIATION TRANSFER FUNCTION; and WIPO PCT Publication No. WO 01/30236 (corresponding to U.S. patent application Ser. No. 09/427,178), published May 3, 2001, titled SOLID-STATE NON-INVASIVE THERMAL CYCLING SPECTROMETER. The entire disclosures of all of the above-mentioned patents, patent applications and publications re hereby incorporated by reference herein and made a part of this specification.

Figure 25:
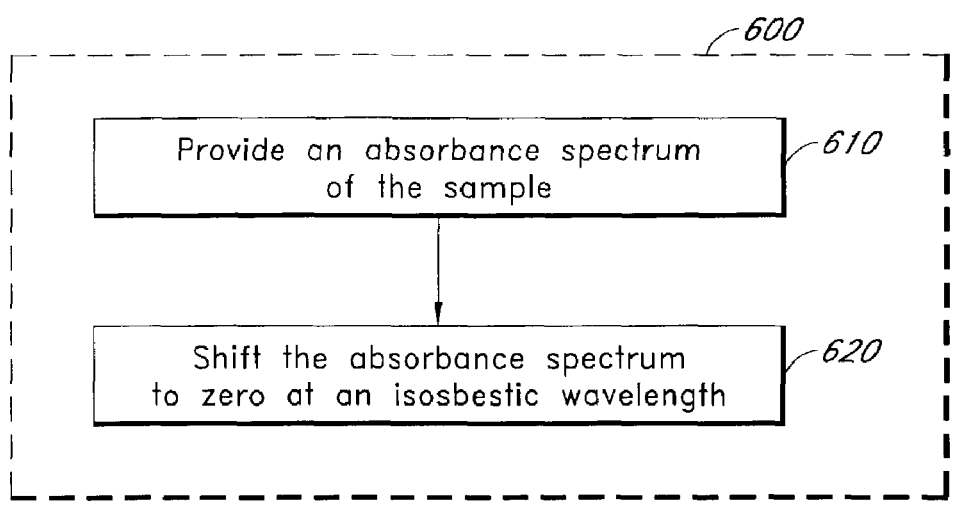
FIG. 25 is a flow diagram of one embodiment of a method of providing pathlength insensitive measurements of blood constituents in a sample using infrared (IR) spectroscopy.

FIG. 25 is a flow diagram of one embodiment of a method 600 of providing pathlength insensitive measurements of blood constituents in a sample using IR spectroscopy. In an operational block 610, the method 600 comprises providing an absorbance spectrum of the sample. In an operational block 620, the method 600 further comprises shifting the absorbance spectrum to zero at an isosbestic wavelength. Water and a protein within the sample have approximately equivalent absorptions at the isosbestic wavelength.

Various embodiments of the present invention have been described above. Although this invention has been described with reference to these specific embodiments, the descriptions are intended to be illustrative of the invention and are not intended to be limiting. Various modifications and applications may occur to those skilled in the art without departing from the true spirit and scope of the invention as defined in the appended claims.

What is claimed is:

1. A method of measuring concentration of glucose in a fluid sample comprising, in no particular order:
   providing a cuvette;
   providing a source of electromagnetic radiation that emits radiation through the cuvette;
   providing a detector that detects radiation emitted from the source, the detection occurring after the radiation has traveled a pathlength, traveling a pathlength comprising passing at least through the cuvette;
   inserting saline reference fluid into the cuvette;
   using the saline reference fluid to determine the pathlength;
   using the pathlength to determine the correct reference spectrum for sample water absorbance, and calculating the correct reference spectrum for sample water absorbance or selecting the correct reference spectrum for sample water absorbance from among a plurality of stored reference spectra;
   using the pathlength to determine the correct reference spectrum for sample protein absorbance, and calculating the correct reference spectrum for sample protein absorbance or selecting the correct reference spectrum for sample protein absorbance from among a plurality of stored reference spectra;
   inserting a fluid sample into the cuvette;
   emitting a range of wavelengths from the source through the cuvette and the fluid sample;
   obtaining total sample absorbance data by measuring, through the range of wavelengths, the amount of radiation that reaches the detector;
   subtracting the correct reference water and protein absorbance spectra from the total sample absorbance data; and
   using the remaining absorbance spectrum, after the correct reference water and protein absorbance spectra have been subtracted, to determine concentration of glucose in the fluid sample.

2. The method of claim 1, wherein the emitter emits electromagnetic radiation in the infrared range.

3. The method of claim 1, wherein the correct reference water absorbance spectra is subtracted from the total sample absorbance data before the correct reference protein absorbance spectra is subtracted from the total sample absorbance data.

4. The method of claim 1, wherein the pathlength is determined based on water absorbance for wavelengths between approximately 4.5 and approximately 5 micrometers.

5. The method of claim 1, wherein the range of wavelengths comprises more than one wavelength.

6. The method of claim 1, wherein the correct water absorbance reference spectrum comprises the absorption rate of water at more than one wavelength for the given pathlength.

7. The method of claim 1, wherein the correct water absorbance reference spectrum is determined using an absorbance peak at approximately 4.7 micrometers.

8. The method of claim 1, wherein confirmation that the correct water absorbance reference spectrum has been subtracted is obtained by determination that there is zero residual absorbance in the wavelengths between approximately 4.5 and approximately 5 micrometers.

9. The method of claim 1, wherein the correct protein absorbance reference spectrum comprises the absorption rate of protein at more than one wavelength for the given pathlength.

10. The method of claim 1, wherein the correct protein absorbance reference spectrum is determined using an absorbance peak between approximately 7.0 and approximately 7.2 micrometers.

11. The method of claim 1, wherein the correct protein absorbance reference spectrum is determined using an absorbance peak between approximately 7.9 and approximately 8.1 micrometers.

12. The method of claim 1, wherein absorbance spectra are obtained using a Fourier-Transform Infrared instrument.

13. The method of claim 1, wherein the concentration of glucose is determined using an absorbance peak at approximately 9.25 micrometers.

14. The method of claim 1, wherein the concentration of glucose is determined using an absorbance peak at approximately 9.65 micrometers.

15. A method of measuring concentration of an analyte in a fluid sample comprising, in no particular order:
   providing a sample container;
   providing a source of electromagnetic radiation that emits radiation through the sample container;
   providing a detector of electromagnetic radiation that detects radiation emitted from the source after the radiation has traveled a pathlength, traveling a path length comprising passing at least through the sample container;
   inserting a reference fluid into the sample container;
   determining the pathlength;
   using the pathlength to determine the correct reference spectrum for sample water absorbance;
   inserting a fluid sample into the sample container;
   emitting at least one wavelength from the source through the sample container and the fluid sample;
   obtaining composite sample data by measuring the amount of radiation of the at least one wavelength that reaches the detector;
   subtracting the correct water absorbance reference spectrum from the composite sample data; and
   using the remaining absorbance spectrum, after the correct water absorbance reference spectrum has been subtracted, to determine concentration of the analyte in the fluid sample.

16. The method of claim 15, further comprising:
   using the pathlength to determine the correct reference spectrum for sample protein absorbance;
   subtracting the correct protein absorbance reference spectrum from the composite sample data; and
   using the remaining absorbance spectrum, after the correct protein absorbance reference spectrum has been subtracted, to determine concentration of the analyte in the fluid sample.

17. The method of claim 15, wherein the analyte is Glucose.

18. The method of claim 15, wherein the sample container is a cuvette.

19. The method of claim 15, wherein the emitter emits electromagnetic radiation in the infrared range.

20. The method of claim 15, wherein the pathlength is determined using a fringe pattern of the fluid container when the container is empty.

21. The method of claim 15, wherein the pathlength is determined by measuring the absorbance of the reference fluid.

22. The method of claim 21, wherein the pathlength determination is made both before and after composite sample data has been obtained.

23. The method of claim 21, wherein the reference fluid is water.

24. The method of claim 21, wherein the reference fluid is saline solution.

25. The method of claim 15, wherein the pathlength is determined based on water absorbance for a wavelength in the range of approximately 4.5 to approximately 5 micrometers.

26. The method of claim 15, wherein the range of wavelengths comprises more than one wavelength.

27. The method of claim 15, wherein the range of wavelengths comprises at least one discreet wavelength.

28. The method of claim 15, wherein the correct water absorbance reference spectrum comprises the absorption rate of water at more than one wavelength for the given pathlength.

29. The method of claim 15, wherein the correct water absorbance reference spectrum comprises at least one absorbance value at or near a reference water wavelength.

30. The method of claim 15, wherein the correct water absorbance reference spectrum is determined using an absorbance peak at approximately 4.7 micrometers.

31. The method of claim 15, wherein confirmation that the correct water absorbance reference spectrum has been subtracted is obtained by determination that there is zero residual absorbance in the wavelengths between approximately 4.5 and approximately 5 micrometers.

32. The method of claim 15, wherein the correct protein absorbance reference spectrum comprises the absorption rate of protein at more than one wavelength for the given pathlength.

33. The method of claim 15, wherein the correct protein absorbance reference spectrum comprises the absorption rate of protein at more than one wavelength for the given pathlength.

34. The method of claim 15, wherein the correct protein absorbance reference spectrum comprises at least one absorbance value at or near a reference protein wavelength.

35. The method of claim 15, wherein the correct protein absorbance reference spectrum is determined using an absorbance peak between approximately 7.0 and approximately 7.2 micrometers.

36. The method of claim 15, wherein the correct protein absorbance reference spectrum is determined using an absorbance peak between approximately 7.9 and approximately 8.1 micrometers.

37. The method of claim 15, wherein absorbance spectra are obtained using a Fourier-Transform Infrared instrument.

38. The method of claim 15, wherein the analyte is glucose.

39. The method of claim 38, wherein the concentration of the analyte is determined using an absorbance peak at approximately 9.25 micrometers.

40. The method of claim 38, wherein the concentration of the analyte is determined using an absorbance peak at approximately 9.65 micrometers.

41. A method of measuring concentration of an analyte in a fluid sample comprising, in no particular order:
    providing a sample container;
    providing a source of electromagnetic radiation that emits radiation through the sample container;
    providing a detector of electromagnetic radiation that detects radiation emitted from the source after the radiation has traveled a pathlength, traveling a pathlength comprising passing at least through the sample container;
    inserting a reference fluid into the sample container;
    determining the pathlength;
    using the pathlength to determine the correct reference spectrum for sample water absorbance, the reference spectrum for sample water absorbance comprising at least one absorbance value at or near a reference water wavelength;
    inserting a fluid sample into the sample container;
    emitting at least one wavelength from the source through the sample container and the fluid sample;
    obtaining composite sample data by measuring the amount of the at least one wavelength of radiation that reaches the detector; and
    subtracting the correct water absorbance reference spectrum from the composite sample data; and
    using the remaining absorbance spectrum, after the correct water absorbance reference spectrum has been subtracted, to determine concentration of the analyte in the fluid sample.

42. The method of claim 41, further comprising:
    using the pathlength to determine the correct reference spectrum for sample protein absorbance, the reference spectrum for sample protein absorbance comprising at least one absorbance value at or near a reference protein wavelength;
    subtracting the correct protein absorbance reference spectrum from the composite sample data; and
    using the remaining absorbance spectrum, after the correct protein absorbance reference spectrum has been subtracted, to determine concentration of the analyte in the fluid sample.

43. The method of claim 41, wherein at least one of the reference water wavelengths is approximately 4.7 micrometers.

44. The method of claim 41, wherein at least one of the reference protein wavelengths is approximately 7.1 micrometers.

45. The method of claim 41, wherein at least one of the reference protein wavelengths is approximately 8.0 micrometers.

* * * * *

UNITED STATES PATENT AND TRADEMARK OFFICE
Certificate

Patent No. 7,009,180 B2                                                  Patented: March 7, 2006

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Bernhard B. Sterling, Danville, CA (US); James R. Braig, Piedmont, CA (US); Philip C. Hartstein, San Francisco, CA (US); and Kenneth G. Witte, San Jose, CA (US).

Signed and Sealed this Twenty-third Day of December 2008.

DAVID P. PORTA
*Supervisory Patent Examiner*
Art Unit 2884

UNITED STATES PATENT AND TRADEMARK OFFICE
CERTIFICATE OF CORRECTION

PATENT NO.       : 7,009,180 B2
APPLICATION NO.  : 10/319409
DATED            : March 7, 2006
INVENTOR(S)      : Sterling et al.

It is certified that error appears in the above-identified patent and that said Letters Patent is hereby corrected as shown below:

Title Page; item (56);

Page 2, Column 1, Line 29, After "6,862,534" delete "B1" and insert --B2--, therefor.

Page 2, Column 2, Line 16, delete "et al," and insert --et al.,--, therefor.

Sheet 12 of 28, Reference numeral 70, Line 2, delete "Sysytem" and insert --System--, therefor.

Sheet 12 of 28, Reference numeral 72, Line 2, delete "Sysytem" and insert --System--, therefor.

Sheet 12 of 28, Reference numeral 77, Line 2, delete "77" and insert --77--, therefor.

Column 1, Line 59, Before "protein" insert --a--.

Column 13, Line 36, After "possible" insert --.--.

Column 22, Line 55, Delete ""wholeblood"" and insert --"whole-blood"--, therefor.

Column 23, Line 45, Delete "electro-magnetic" and insert --electromagnetic--, therefor.

Column 23, Line 48, Delete "20.0 m;" and insert --20.0µm;--, therefor.

Column 26, Line 11, Delete "side.)" and insert --side).--, therefor.

Column 28, Line 51, Delete "subtracing" and insert --subtracting--, therefor.

Column 29, Line 2, After "to" insert --be--.

UNITED STATES PATENT AND TRADEMARK OFFICE
CERTIFICATE OF CORRECTION

PATENT NO. : 7,009,180 B2
APPLICATION NO. : 10/319409
DATED : March 7, 2006
INVENTOR(S) : Sterling et al.

It is certified that error appears in the above-identified patent and that said Letters Patent is hereby corrected as shown below:

Column 32, Line 36-37, In Claim 15, delete "path length" and insert --pathlength--, therefor.

Signed and Sealed this

Twentieth Day of January, 2009

JON W. DUDAS
*Director of the United States Patent and Trademark Office*